(12) United States Patent
Liaw

(10) Patent No.: US 7,700,113 B2
(45) Date of Patent: Apr. 20, 2010

(54) INHIBITING BREAST CANCER CELL GROWTH BY ADMINISTERING AN INTRACELLULAR DOMAIN OF NOTCH2

(75) Inventor: Lucy Liaw, South Portland, ME (US)

(73) Assignee: Maine Medical Research Institute, a division of Maine Medical Center, Scarborough, ME (US)

( * ) Notice: Subject to any disclaimer, the term of this patent is extended or adjusted under 35 U.S.C. 154(b) by 0 days.

(21) Appl. No.: 11/975,522

(22) Filed: Oct. 19, 2007

(65) Prior Publication Data

US 2008/0112940 A1 May 15, 2008

Related U.S. Application Data

(60) Provisional application No. 60/852,749, filed on Oct. 19, 2006.

(51) Int. Cl.
*A61K 38/17* (2006.01)
*A61K 38/18* (2006.01)
*C07K 14/435* (2006.01)
*C07K 14/475* (2006.01)

(52) U.S. Cl. .............................. 424/198.1; 424/195.11; 514/2; 514/12; 530/350

(58) Field of Classification Search ........................ None
See application file for complete search history.

(56) References Cited

U.S. PATENT DOCUMENTS 5,750,652 A * 5/1998 Artavanis-Tsakonas et al. .. 530/350

FOREIGN PATENT DOCUMENTS

WO   WO 9407474 A1 *  4/1994

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*

O'Neill et al. Notch2 signaling induces apoptosis and inhibits human MDA-MB-231 Xenograft growth. Am J Pathol 171(3): 1023-1036, 2007.*
Artavanis-Tsakonas et al., 1991, Trends Genet. 7:403-408.
Artavanis-Tsakonas et al., 1995, Science 268:225-232.
Callahan et al., J. Mammary Gland Biol Neoplasia., 2004, 9:145-163.
Capobianco et al., 1997, Mol. Cell Biol., 17:6265-6273.
Coffman et al., 1993, Cell 73:659-671.
Conlon et al., 1995, Development 121: 1533-1545.
Curry et al., Mol. Cancer Ther., 2007, 6:1983-1992.
Ellisen et al., 1991, Cell 66:649-661.
Fortini and Artavanis-Tsakonas, 1993, Cell 75:1245-1247.
Franco del Amo et al., 1992, Development 115:737-744.
Franklin et al., 1999, Curr. Biol. 9:1448-1457.
Gallahan et al., 1996, Cancer Res., 56:1775-1785.
Greenwald and Rubin, 1992, Cell 68:271-281.
Gurdon, 1992, Cell 68:185-199.
Hamada et al., 1999, Development 126: 3415-3424.
Han et al., 2000, Blood 95:1616-1625.
Hicks et al., 2002, J. Neurosci. Res. 68:655-667.
Hu et al., 2006, Am. J. Pathol. 168:973-990.
Hukriede et al., 1997, Development 124:3427-3437.
Ikeuchi and Sisodia, 2003, J. Biol. Chem. 278:7751-7754.
Jarriault et al., 1995, Nature 377, 355-358.
Jhappan et al., 1992, Genes Dev., 6:345-355.
Jiang et al., 1998, Genes Dev. 12: 1046-1057.
Joutel et al., 1996, Nature 383: 707-710.
Kadesch, 2000, Exp. Cell. Res. 260:1-8.
Klueg et al., 1998, Mol. Biol. Cell 9:1709-1723.
Krebs et al., 2000, Genes Dev. 14: 1343-1352.
Lardelli et al., 1993, Mech. Dev. 46:123-136.
Li et al., 1997, Nat. Genet. 16: 243-251.
Li, et al., 1998, Immunity 8:43-55.
Maillard et al., 2003, Immunity 19:781-791.
Massi et al., Modern Pathology, 2006, 19:246-254.
Morrissette et al., 2001, Hum. Mol. Genet. 10:405-413.
Muskavitch and Hoffmann, 1990, Curr. Top. Dev. Biol. 24:289-328.
Nofziger et al., 1999, Development 126, 1689-1702.
Nye et al., 1994, Development 120:2421-2430.
Parr, et al., 2004, Int. J. Mol. Med. 14:779-786.
Pear et al., 1996, J. Exp. Med., 183:2283-2291.
Qi et al., 1999, Science 283:91-94.
Radtke and Raj, 2003, Nat. Rev. Cancer 3:756-767.
Rae et al., 2000, Int. J. Cancer 88: 726-732.
Reaume et al., 1992, Dev. Biol. 154:377-387.
Reedijik et al., 2005, Cancer Res., 65:8530-8537.
Rohn et al., 1996, J. Virol. 70: 8071-8080.
Small et al., 2001, J. Biol. Chem. 276: 32022-32030.
Small et al., 2003, J. Biol. Chem. 278:16405-16413.
Smith et al., 1995, Cell Growth Differ., 6:563-577.
Sun and Artavanis-Tsakonas, 1996, Development 122:2465-2474.

(Continued)

*Primary Examiner*—Bridget E Bunner
(74) *Attorney, Agent, or Firm*—Drinker Biddle & Reath LLP

(57) ABSTRACT

The present invention relates to the ability of constitutively active Notch 2 to function as an inhibitor of breast cancer. The invention provides methods and compositions for inhibiting breast cancer cells by using hNotch2ICD polypeptides.

2 Claims, 8 Drawing Sheets

OTHER PUBLICATIONS van der Pluijim et al., 2001, Am. J. Phathol. 159:971-982.
Varnum-Finney et al., 1998, Blood 91:4084-4091.
Varnum-Finney et al., 2000, J. Cell Sci. 113 Pt 23:4313-4318.
Weinmaster et al., 1991, Development 113:199-205.
Weinmaster et al., 1992, Development 116:931-941.
Weinmaster, 1998, Curr. Opin. Genet. Dev. 8, 436-442.
Weintraub, 1993, Cell 75:1241-1244.
Xue et al., 1999 Hum. Mol. Genet. 8: 723-730.
Zagouras et al., 1995, Proc. Natl. Acad. Sci. USA 92: 6414-6418.
Zhou et al., 2000, Mol. Cell Biol. 20, 2400-2410.
Zimrin et al., 1996, J. Biol. Chem. 271:32499-32502.
Eiriksdottir, et al., "Cellular Uptake of Cell-Penetrating Peptides," *Drug Design Reviews* pp. 161-173, 2004.
Ferrari, et al., "Caveolae-Mediated Internalization of Extracellular HIV-1 Tat Fusion Proteins Visualized in Real Time," *Molecular Therapy*, 8(2) pp. 284-294, 2003.
Hawiger, et al., "Noninvasive intracellular delivery of functional peptides and proteins," *Curr Opin Chem. Biol.*, 3(1) pp. 89-94, 1999.
Kim, et al., "Cytoplasmic transduction peptide (CTP): new approach for the delivery of biomolecules into cytoplasm in vitro and in vivo," *Exp Cell Res.* 312 (8) pp. 1277-1288, 2006.
Nair, et al., "NLSdb: database of nuclear localization signals," *Nucleic Acids Research*, 31 (1) pp. 397-399, 2003.
Schwartz, et al., "Peptide-mediated cellular delivery," *Curr Opin in Moe Ther*, 2 (2) pp. 162-167, 2000.

* cited by examiner

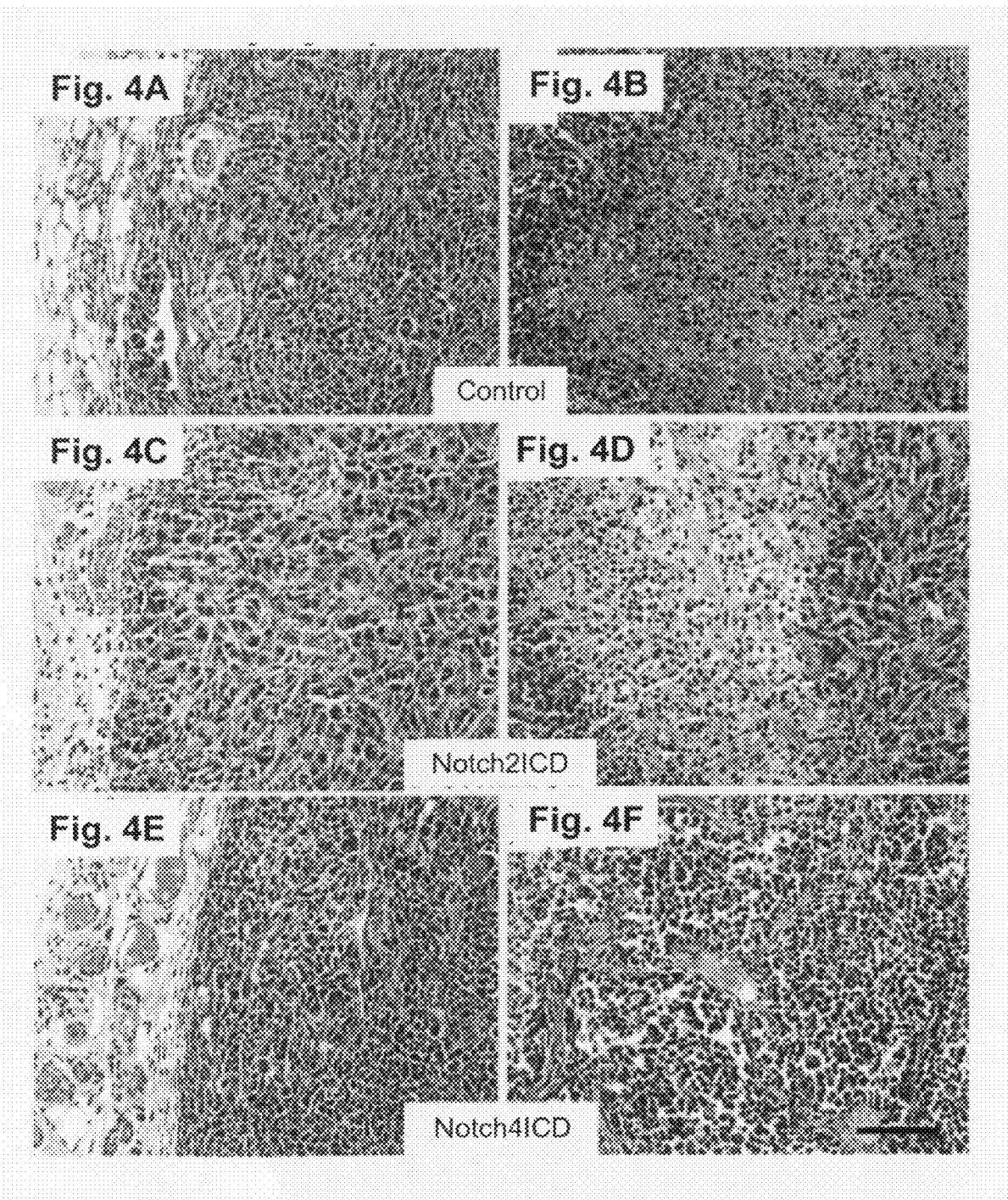

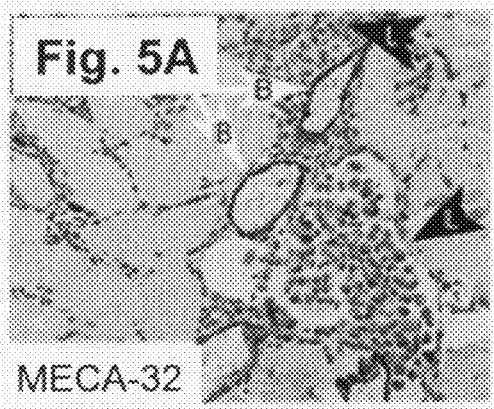
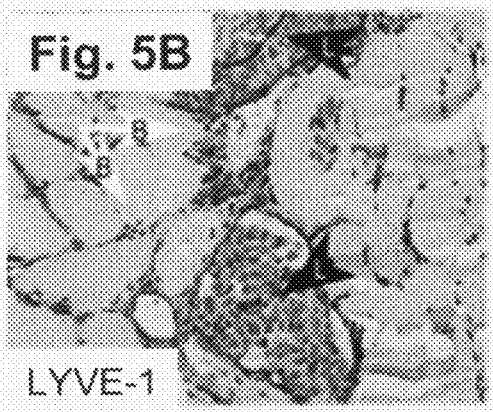
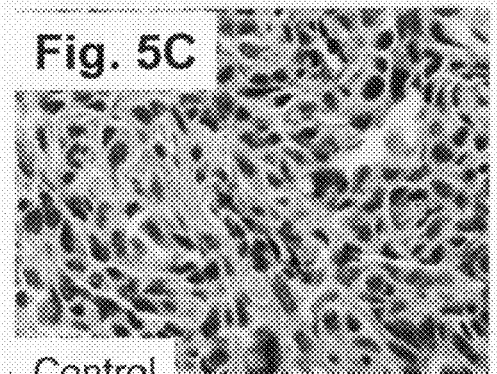
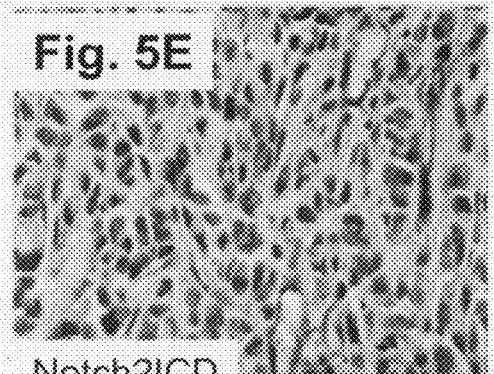
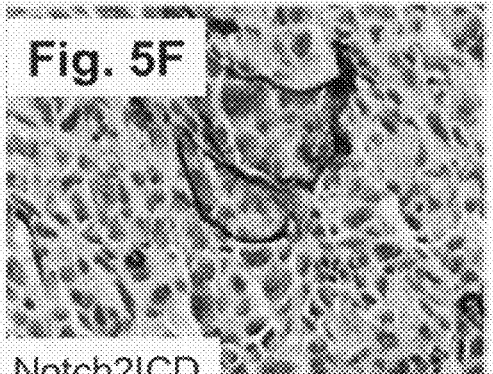
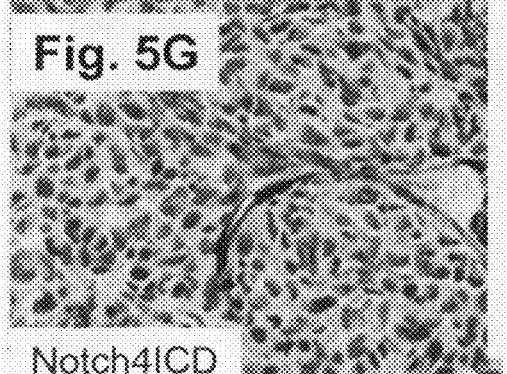
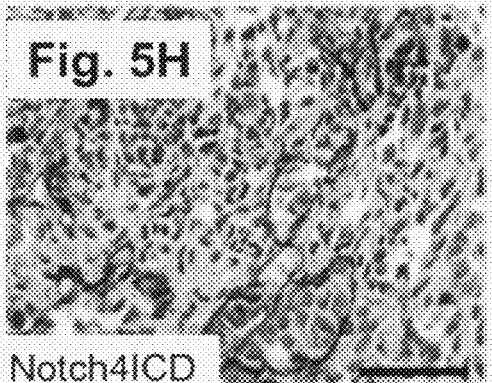

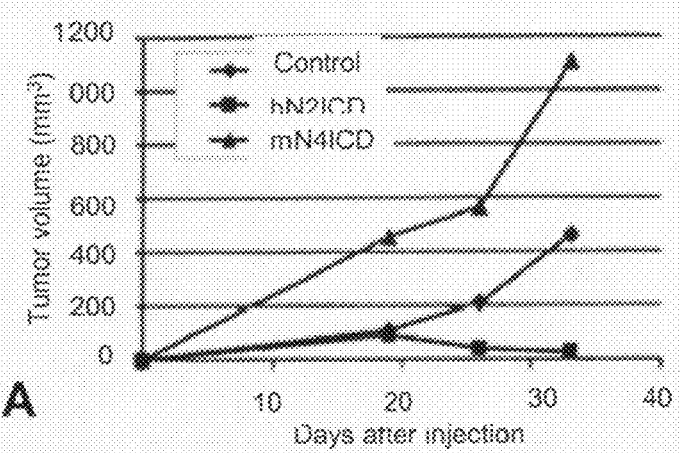
Fig. 7A
Tumor periphery | Tumor core
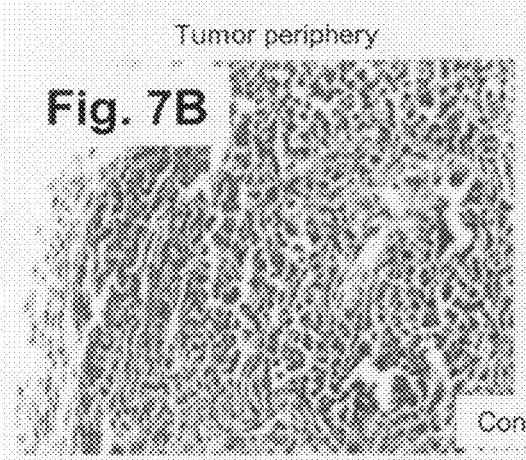 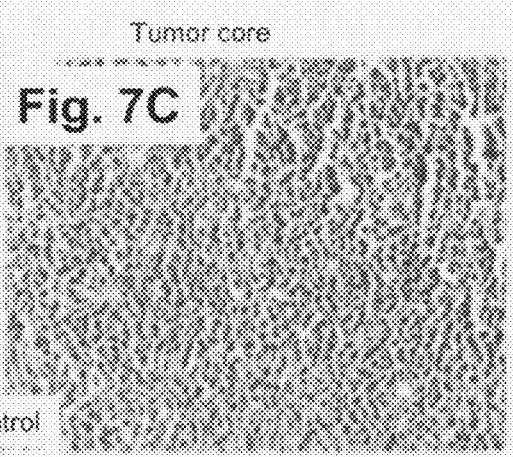
Fig. 7B — Fig. 7C — Control
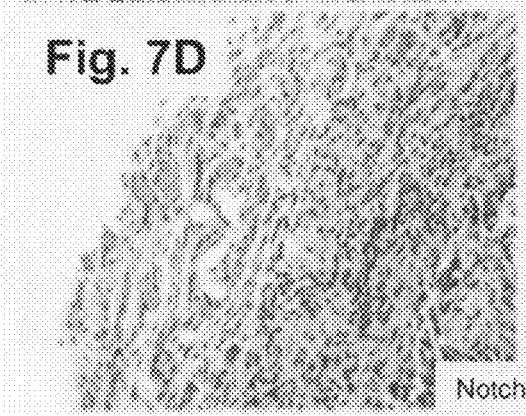 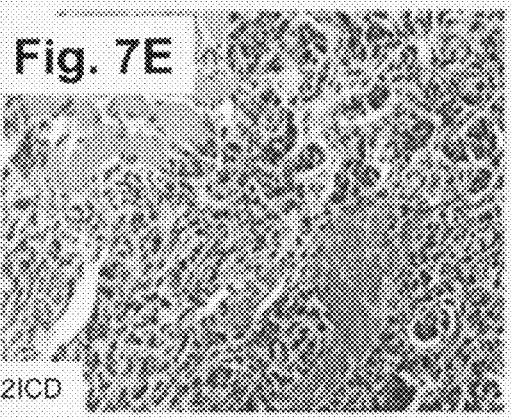
Fig. 7D — Fig. 7E — Notch2ICD
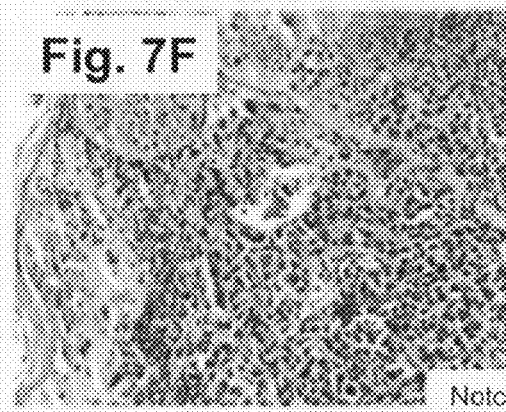 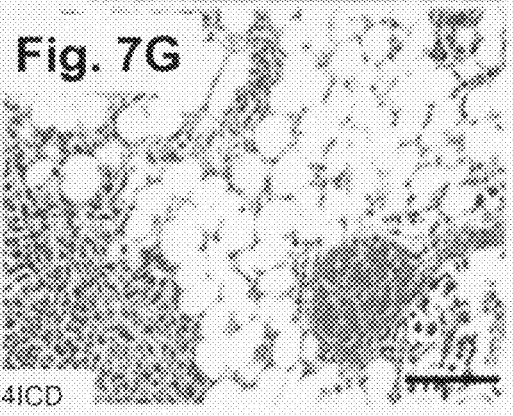
Fig. 7F — Fig. 7G — Notch4ICD

INHIBITING BREAST CANCER CELL GROWTH BY ADMINISTERING AN INTRACELLULAR DOMAIN OF NOTCH2

CROSS-REFERENCE TO RELATED APPLICATIONS

The present application is entitled to priority under 35 U.S.C. §119(e), to U.S. Provisional Application No. 60/852,749 filed on Oct. 19, 2006, which application is hereby incorporated herein by reference in its entirety.

STATEMENT REGARDING FEDERALLY SPONSORED RESEARCH OR DEVELOPMENT

This invention was made, in part, using funds obtained form the U.S. Government (National Institutes of Health Grant Nos. RO1HL070865, P20RR15555, and P20RR018789), and the U.S. Government therefore has certain rights in this invention.

BACKGROUND OF THE INVENTION

The Notch signaling pathway and its components are highly conserved in all Metazoans, from *Drosophila* to humans. The signaling pathway comprises the Notch receptors and their ligands, all single-pass transmembrane proteins with conserved protein structures (Lardelli, 1994, Mech. Dev. 46, 123-1365). Additional elements of the pathway include positive and negative modifiers as well as transcription factors. Notch receptors transduce essential developmental signals between neighboring cells by forming a complex that leads to the transcription of target genes upon activation. Neighboring cells expressing various Notch ligands and receptors amplify and consolidate molecular differences, eventually dictating cell fates and implementing developmental programs of differentiation, proliferation and apoptosis.

In mammals, Notch genes encode four large Type I transmembrane proteins called Notch receptors (Notch 1, Notch 2, Notch 3 and Notch 4) comprised of multiple known structural motifs. En route to the cell surface, the Notch receptor is proteolytically cleaved by furin-like convertases in the trans-Golgi network, giving rise to two subunits of the mature receptor. The extracellular Notch subunit (ECN) consists largely of a ligand-binding domain composed of small, tandem cysteine knot motifs called epidermal growth factor (EGF)-like repeats (Coffman, 1990, Science 249:1438-1441; Ellisen, 1991, Cell 66:649-661; Weinmaster, 1991, Development 113:199-205; Weinmaster, 1992, Development 116:931-941; Franco del Amo, 1992, Development 115:737-744; Reaume, 1992, Dev. Biol. 154:377-387; Lardelli and Lendahi, 1993, Mech. Dev. 46:123-136; Bierkamp and Campos-Ortega, 1993, Mech. Dev. 43:87-100; Lardelli, 1994, Exp. Cell Res. 204:364-372). In addition to the thirty-six EGF repeats within the extracellular domain of Notch 1, there is a cys-rich domain composed of three Notch Lin Glp (NLG) repeats, which is important for ligand function. This is followed by a cys-poor region between the transmembrane and NLG domain and three LIN 12/Notch repeats that restrain inappropriate, ligand-independent receptor activation.

The transmembrane Notch subunit (NTM) includes a short extracellular domain, a single transmembrane domain, and a large intracellular domain comprised of a an N-terminal domain called the RBP-jkappa associated domain (RAM) and seven iterated cdc10/ankyrin-like repeats positioned between two nuclear localization signals (NLS) (Artavanis-Tsakonas et al., 1995, Science 268:225-232). The ankyrin-like repeat motif is found in many functionally diverse proteins (see, e.g., Bork, 1993, Proteins 17:363-374), including members of the Rel/NF-κB family (Blank, 1992, TIBS 17:135-140), and is thought to be responsible for protein-protein interactions. Lastly, the C-terminal PEST domain is involved in proteosome-mediated Notch degradation and thereby regulates the termination of signaling. In addition, mammalian Notch 1, 2, and 3 contain cytokine response (NCR) regions while Notch 1 and 2 have C-terminal transcriptional activation domains (TAD).

The ligands for the Notch receptors have traditionally been divided into two subclasses, Delta-like and Serrate-like, defined by the absence and presence, respectively, of an additional cysteine-rich domain in the extracellular portion of the polypeptide (Weinmaster, 1998, Curr. Opin. Genet. Dev. 8, 436-442, Zimrin, 1996, J. Biol. Chem. 271, 32499-32502).

Several Notch ligands have been identified in vertebrates, including Delta, Serrate and Jagged. The Notch ligands are also transmembrane proteins, having highly conserved structures. These ligands are known to signal cell fate and pattern formation decisions through the binding to the Lin-12/Notch family of transmembrane receptors (Muskavitch and Hoffmann, 1990, Curr. Top. Dev. Biol. 24:289-328; Artavanis-Tsakonas and Simpson, 1991, Trends Genet. 7:403-408; Greenwald and Rubin, 1992, Cell 68:271-281; Gurdon, 1992, Cell 68:185-199; Fortini and Artavanis-Tsakonas, 1993, Cell 75:1245-1247; and Weintraub, 1993, Cell 75:1241-1244). A related protein, the Suppressor of hairless (Su(H)), when co-expressed with Notch in *Drosophila* cells, is sequestered in the cytosol, but is translocated to the nucleus when Notch binds to its ligand Delta (Fortini and Artavanis-Tsakonas, 1993, Cell 75:1245-1247). Studies with constitutively activated Notch proteins missing their extracellular domains have shown that activated Notch suppresses neurogenic and mesodermal differentiation (Coffman, 1993, Cell 73:659-671; Nye, 1994, Development 120:2421-2430).

The mechanism of Notch receptor signaling has been extensively studied and involves the activation of CSL (for CBF1 in mammals, Supressor of Hairless (Su[H]) in *Drosophila* and *Xenopus* and Lag-1 in *Caenorhabditis elegans*)-dependent transcription mediated by the nuclear translocation of the intracellular domain of Notch (Jarriault, 1995, Nature 377, 355-358). Notch displaces corepressors on CSL, changing its function from a repressor into an activator leading to elevated expression of specific genes. Several such targeted genes have been identified and include HES1, a member of the Hairy Enhancer of Split and Hairy Enhancer of Split-Related Proteins families of basic helix-loop-helix transcription factors (Zhou, 2000, Mol. Cell Biol. 20, 2400-2410). However, recent evidence also suggests that Notch signaling may proceed in a CSL-independent manner including pathways utilizing the cytoplasmic protein, Deltex (Small, 2001, J. Biol. Chem. 276, 32022-32030, Nofziger, 1999, Development 126, 1689-1702).

The existence of soluble forms of Notch ligands including the extracellular portion of Delta in *Drosophila* and other organisms have been reported but their physiological roles have not been determined (Nofziger, 1999, Development 126:1689-1702; Franklin, 1999, Curr. Biol. 9:1448-1457; Hukriede, 1997, Development 124:3427-3437; Han, 2000, Blood 95:1616-1625; Klueg, 1998, Mol. Biol. Cell 9:1709-1723; Morrissette, 2001, Hum. Mol. Genet. 10:405-413; Sun, 1996, Development 122:2465-2474). Transcripts encoding the extracellular domain of the Jagged1 ligand have also been detected in human endothelial cells (Zimrin, 1996, J. Biol. Chem. 271:32499-32502). There is evidence that the Delta ligand can be proteolytically cleaved by Kuzbanian, a member of the ADAM family metalloproteases, to generate a soluble extracellular form (Qi, 1999, Science 283; 91-94), and recent data also suggest that the Notch ligands may be processed by the γ-secretase presenilin in a manner similar to the Notch receptor (Ikeuchi, 2003, J. Biol. Chem. 278:7751-7754).

While studies have suggested that the soluble forms of the Notch ligands are able to activate Notch receptors (Han et al., 2000, Blood 95:1616-1625; Qi et al., 1999, Science 283:91-94; Li, et al., 1998, Immunity 8:43-55), there are numerous reports that the soluble forms of the Notch ligands act as antagonists of Notch signaling by impeding the interaction between Notch receptors and their full-length ligands (Small et al., 2001, J. Biol. Chem. 276:32022-32030; Hukriede et al., 1997, Development 124:3427-3437; Varnum-Finney et al., 1998, Blood 91:4084-4091). Secreted forms of Delta perturb association between full length Delta and Notch (Hicks et al., 2002, J. Neurosci. Res. 68:655-667), and inhibit the Notch-dependent repression of myoblast (Varnum-Finney et al., 2000, J. Cell Sci. 113 Pt 23:4313-4318) and hematopoietic progenitor cell (Han et al., 2000, Blood 95:1616-1625) differentiation in vitro. Likewise, the expression of a non-transmembrane form of the Notch ligand, Jagged1(sj1) also antagonizes Notch signaling in NIH 3T3 cells and induces significant changes in their cellular phenotype including FGFR1-dependent transformation (Small et al., 2001, J. Biol. Chem. 276: 32022-32030; Small et al., 2003, J. Biol. Chem. 278:16405-16413).

Notch signaling plays a key role in normal development through diverse effects on differentiation, survival, and proliferation. These events are highly dependent on signal strength and cellular context (Artavanis-Tsakonas, 1995, Science 268:225-232; Kadesch, T., 2000, Exp. Cell. Res. 260:1-8). Phenotypic analysis of mice null for Notch receptors or their ligands emphasizes the requirement for proper Notch signaling not only during development but in the adult as well (Conlon, 1995, Development 121: 1533-1545; Hamada, 1999, Development 126: 3415-3424; Jiang, 1998, Genes Dev. 12: 1046-1057; Krebs, 2000, Genes Dev. 14: 1343-1352; Xue, 1999 Hum. Mol. Genet. 8: 723-730). Indeed, aberrant Notch signaling has been implicated in several human pathological conditions including the development of the CADASIL (Joutel, 1996, Nature 383: 707-710) and Alagille syndromes (Li, 1997, Nat. Genet. 16: 243-251; Li, 1997, Nat. Genet. 16: 243-251) and the formation of neoplasias in mice and humans (Rae, 2000, Int. J. Cancer 88: 726-732; Rohn, 1996, J. Virol. 70: 8071-8080; Zagouras, 1995, Proc. Natl. Acad. Sci. USA 92: 6414-6418).

The impact of Notch signaling on cell fate and proliferation is determined by cell specific context of its activity. Aberrant Notch signaling can initiate an oncogenic pathway that leads to malignant cell transformation (Maillard, 2003, Immunity 19:781-791; Radtke, 2003, Nat. Rev. Cancer 3:756-767) and tumorigenesis, for example in human T lymphoblastic leukemia (Artavanis-Tsakonas, 1995, Science, 268:225-232), hematopoietic cells (Pear, 1996, J. Exp. Med., 183:2283-2291) and thymic lymphoma (Capobianco, 1997, Mol. Cell Biol., 17:6265-6273). In mammary gland, the transforming effect of Notch4 by virtue of MMTV integration (Jhappan, 1992, Genes Dev., 6:345-355; Smith, 1995, Cell Growth Differ., 6:563-577; Gallahan, 1996, Cancer Res., 56:1775-1785), as well as Notch1ICD and Notch3ICD tumorigenesis in mammary gland have been well documented (Hu, 2006, Am. J. Pathol. 168:973-990).

The earliest events in the pathogenesis of breast cancer typically involve the loss of a normal growth regulatory mechanism by a ductal or lobular epithelial cell. Progression of the disease through the stages of intraductal proliferation to invasive carcinoma, and then to metastatic disease, appears to require additional alterations in growth-regulatory pathways. A substantial body of evidence now supports the idea that these alterations in growth regulation result from genetic events, such as point mutation, deletion, and gene amplification.

One clinical goal is to characterize genetic alterations in breast tumors at the various stages of tumor progression. If metastasis requires additional genetic events beyond those responsible for the intraductal and invasive components of the tumor, one should find genetic alterations in the metastasis that are not present in primary tumor. Alternatively, there may be certain genetic lesions that occur early in tumor development that can predispose a tumor to metastasize without the acquisition of additional genetic defects. The identification of such a lesion would provide an important prognostic indicator, because it would provide a means for predicting the likelihood of the development of metastatic disease in tumors identified at an early stage. The characterization of genetic changes present in individual tumor components thus offers the possibility of identifying new prognostic indicators, as well as helping to elucidate the significance of genetic events to tumor progression.

Notch1, Notch 4 and Jagged 1 have all been found to be increased in human breast cancer tissue (Reedijik, 2005, Cancer Res., 65:8530-8537; Callahan, 2004, 9:145-163). Significantly, high expression levels of Jagged1 and Notch1 correlate with poor patient survival (Reedijik, 2005, 65:8530-8537) whereas Par (2004, Int. J. Mol. Med. 14:776-789) reports that a higher level of Notch 2 expression in breast cancer tissue was correlated with a higher chance of survival. In addition Par demonstrates that Notch 2 was highly expressed in well-differentiated tumors, but poorly expressed in breast tumors with poor differentiation.

What is needed in the art is a clarification of the role of Notch in breast cancer, as well as an overall understanding of the genetic events that transform normal breast tissue to malignancy. In particular, the role of Notch 2 in the development and progression is needed, in order to understand whether Notch 2 can become a target for treatment and intervention of the development of breast cancer. The present invention addresses and meets these needs.

BRIEF SUMMARY OF THE INVENTION

The invention includes a method of inhibiting the growth of a breast cancer cell in a mammal having breast cancer, comprising administering to a mammal an isolated polypeptide comprising an intracellular domain of Notch 2, or a biologically active mutant, variant or fragment thereof, wherein the polypeptide inhibits the growth of a breast cancer cell. In an aspect, the polypeptide is human Notch 2 intracellular domain (hNotch2ICD).

In an aspect of the invention, the mammal is a human.

A polypeptide of the invention may further comprise a detectable label.

The invention also includes a method of inhibiting the growth of a breast cancer cell in a mammal having breast cancer, comprising administering to a mammal an isolated nucleic acid encoding hNotch2ICD and expressing hNotch2ICD polynucleotide in a breast cancer cell, wherein the growth of a breast cancer cell is inhibited. In an aspect, a nucleic acid further encodes a detectable label. In another aspect, a nucleic acid is expressed from a vector, wherein the vector comprises at least one regulatory sequence necessary to control expression of the nucleic acid sequence.

The invention also includes a method of diagnosing a Notch 2-related mammary adenocarcinoma, comprising assessing the level of Notch 2 signaling in a first, non-cancerous mammary cell, assessing the level of Notch 2 signaling in a second mammary cell of unknown cancerous state, and comparing the level of Notch 2 signaling in the first and second mammary cells, wherein a lower level of signaling through the Notch 2 pathway in the second cell, when compared to the first cell, is an indication that the second cell is afflicted with mammary adenocarcinoma.

The invention also includes a kit for inhibiting the growth of a breast cancer cell in a mammal diagnosed as having breast cancer, comprising a composition comprising an isolated hNotch2ICD polypeptide as set forth in SEQ ID NO:3, wherein when the polypeptide is administered to a mammal, the growth of the breast cancer cell is inhibited. In an aspect, the polypeptide further comprises a detectable label.

The invention also includes a kit for inhibiting the growth of a breast cancer cell in a mammal diagnosed with breast cancer, the kit comprising a composition comprising an isolated hNotch2ICD nucleic acid, wherein when the nucleic acid is administered to the mammal, the growth of the breast cancer cell is inhibited. In an aspect, the composition further comprises a vector comprising at least one promoter sequence, further wherein the hNotch2ICD nucleic acid comprises the vector. In an aspect, the nucleic acid is linked to a nucleic acid sequence encoding at least one detectable label.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIG. 1A depicts cell lysates analyzed by SDS-PAGE, followed by immunoblot with antibodies directed against Notch1, Notch 2, Notch4, Jagged1 and β-actin as a control. FIG. 1B is a histogram reporting the relative CBF luciferase activity obtained for MDA-MB-231 cell populations expressing either control of activated forms of either Notch 2 or Notch4 receptor. FIG. 1C is a histogram depicting relative HES1 expression levels obtained using quantitative real-time PCR, with expression levels normalized to β-actin obtained for MDA-MB-231 cell populations expressing either control of activated forms of either Notch 2 or Notch4 receptors. FIG. 1D is a histogram depicting relative Hrt1 expression levels detected using quantitative real-time PCR, with expression levels normalized to β-actin obtained for MDA-MB-231 cell populations expressing either control of activated forms of either Notch 2 or Notch4 receptors.

FIG. 2, comprising FIG. 2A is a histogram depicting the percentage of total cells that stain positive for BrdU in control, and cells stably transfected with hN2ICD or mN4ICD. FIG. 2B is a histogram depicting the percentage of total cells stained with TUNEL. FIG. 2C is a series of images of stably transfected control, hNotch2ICD and mNotch4ICD cell populations plated at clonal density in soft agar and stained after 21 days with p-iodonitrotetrazolium. FIG. 2D is a histogram depicting the average number of colonies quantified for the experiments in C. FIG. 2E is a histogram depicting cytokine levels detected using ELISA assay for tumor cell conditioned medium.

FIG. 3, comprising FIG. 3A is a graph depicting the volume of tumors as a function of days post injection for stable MDA-MB-231 cells expressing control, hNotch2ICD and mNotch4ICD. FIG. 3B is a histogram depicting the number of BrdU positive cells for control, hNotch2ICD and mNotch4ICD cells. FIG. 3C is a histogram depicting the number of TUNEL positive cells for the same tumor samples as in B.

FIG. 4, comprising FIGS. 4A-4F, is a series of images depicting tumor histology of the NotchICD xenografts stained with hematoxylin and eosin. FIG. 4 A, FIG. 4C, and FIG. 4E illustrate the tumor periphery and FIG. 4B, FIG. 4D, and FIG. 4F illustrate tumor core.

FIG. 5, comprising FIGS. 5A-5H are a series of images depicting that NotchICD tumor vascularization does not correlate with tumor size. FIG. 5A, FIG. 5C, FIG. 5E and FIG. 5G illustrate MECA-32 immunostaining. FIG. 5B, FIG. 5D, FIG. 5F and FIG. 5H illustrate and LYVE-1 immunostaining. Sections are counterstained with hematoxylin.

FIG. 6, comprising FIG. 6A is a histogram demonstrating that activation of either the Notch 2 or the Notch4 pathway led to increased vascularization. FIG. 6B is a histogram depicting the secreted circulating angiogenic factors in tumor bearing mice using an ELISA assay. FIG. 6C is a series of gels depicting transcript levels of angiogenic cytokines in tumors detected using RT-PCR. Cyclophilin was used as a normalizing control. FIG. 6D is a series of gels depicting host-derived transcripts from tumors detected by RT-PCR.

FIG. 7, comprising FIGS. 7A-7G, is a series of images depicting Notch 2 suppression of xenograft growth in mammary fat pads. FIG. 7A is a graph depicting tumor volume as a function of days post injection. FIG. 7B, FIG. 7C, FIG. 7D, FIG. 7E, FIG. 7F and FIG. 7G are a series of images of tumors collected at the end of the experiment, sectioned and stained with hematoxylin/eosin. FIG. 7B, FIG. 7D and FIG. 7F are images of the tumor periphery. FIG. 7C, FIG. 7E and FIG. 7G are images depicting the tumor core.

DETAILED DESCRIPTION OF THE INVENTION

Figure 1B:
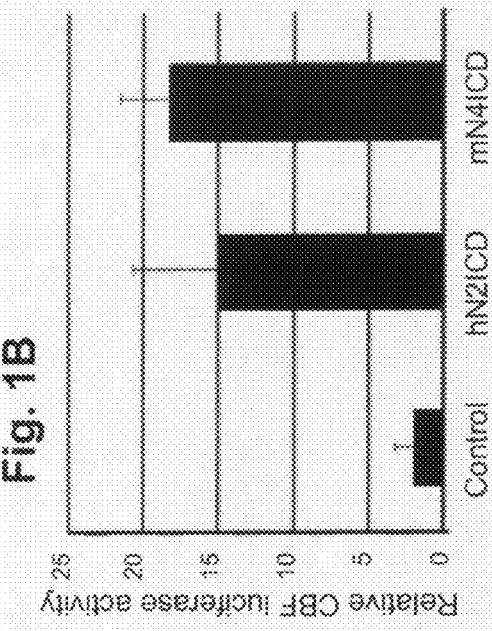
FIGS. 1A-1D, is a series of images illustrating the establishment of a human breast cancer model to study activation of Notch signaling.

The present invention relates to the role that Notch 2 plays as a cancer suppressor. As set forth herein for the first time, constitutive expression of the Notch 2 intracellular domain (Notch2ICD) inhibits breast cancer cell proliferation and survival both in vitro and in vivo. While it is known that Notch signaling can activate either oncogenic or tumor suppressor pathways depending upon the cellular context, the role of Notch 2 as a breast cancer tumor suppressor was heretofore unknown. The present invention also shows that tumor vascularization and growth are separable events of tumor progression. This new understanding of the relationship between Notch signaling pathways and breast cancer proliferation and tumorigenesis encompasses novel methods of evaluating and treating breast cancer.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

"Angiogenesis," as used herein, means the formation of new blood vessels and encompasses the development of angiogenic tissue and/or altered cell or tissue morphology typical of angiogenic tissue development. One skilled in the art would appreciate, based upon the disclosure provided herein, that the level of angiogenesis can be assessed using, for example but not limited to, a CAM assay, a nude mouse in vivo assay, an endothelial cell migration assay to assess sprout formation, the development of chord-like structures, and other methods known in the art.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1988; Houston et al., 1988; Bird et al., 1988).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "cancer" as used herein is defined as disease characterized by the rapid and/or uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

The term "DNA" as used herein is defined as deoxyribonucleic acid.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The use of the term "DNA encoding" should be construed to include the DNA sequence which encodes the desired protein and any necessary 5' or 3' untranslated regions accompanying the actual coding sequence.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 500 nucleotides, even more preferably, at least about 500 nucleotides to about 1000 nucleotides.

As used herein, the term "fragment" as applied to a polypeptide, may ordinarily be at least about seven contiguous amino acids, typically, at least about fifteen contiguous amino acids, more typically, at least about thirty contiguous amino acids, typically at least about forty contiguous amino acids, preferably at least about fifty amino acids, even more preferably at least about sixty amino acids and most preferably, the peptide fragment will be greater than about seventy contiguous amino acids in length.

"Derivatives," and "variants" of the polypeptides of the invention (or of the DNA encoding the same) are peptides which may be altered in one or more amino acids (or in one or more base pairs) such that the peptide (or DNA) is not identical to the sequences recited herein, but has the same property as the peptides disclosed herein, in that the peptide has, by way of one example, the biological activity of a Notch 2 intracellular domain.

The term "polypeptide" as used herein is defined as a chain of amino acid residues, usually having a defined sequence. As used herein the term polypeptide is mutually inclusive of the terms "peptide" and "protein".

"Proliferation" is used herein to refer to the reproduction or multiplication of similar forms of entities, for example proliferation of a cell. That is, proliferation encompasses production of a greater number of cells, and can be measured by, among other things, simply counting the numbers of cells, measuring incorporation of $^3$H-thymidine into the cell, and the like.

As used herein, the term "promoter" or "regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "therapeutic" treatment is a treatment administered to a patient who exhibits signs of pathology for the purpose of diminishing or eliminating those signs and/or decreasing or diminishing the frequency, duration and intensity of the signs.

An "effective amount" of a compound is that amount of compound which is sufficient to provide a detectable effect to a cell to which the compound is administered when compared to an otherwise identical cell to which the compound is not administered.

"Instructional material," as that term is used herein, includes a publication, a recording, a diagram, or any other medium of expression which can be used to communicate the usefulness of the composition and/or compound of the invention in the kit for effecting alleviating or treating the various diseases or disorders recited herein. Optionally, or alternately, the instructional material may describe one or more methods of alleviating the diseases or disorders in a cell or a tissue or a mammal, including as disclosed elsewhere herein.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

A first region of an oligonucleotide "flanks" a second region of the oligonucleotide if the two regions are adjacent to one another or if the two regions are separated by no more than about 1000 nucleotide residues, and preferably no more than about 100 nucleotide residues.

By the term "DNA segment" is meant a molecule comprising a linear stretch of nucleotides wherein the nucleotides are present in a sequence that encodes, through the genetic code, a molecule comprising a linear sequence of amino acid residues that is referred to as a protein, a protein fragment, or a polypeptide.

"Gene," as used herein, refers to a single polypeptide chain or protein, and as used herein includes the 5' and 3' ends. The polypeptide can be encoded by a full-length sequence or any portion of the coding sequence, so long as the functional activity of the protein is retained.

A "complementary DNA" or "cDNA" gene includes recombinant genes synthesized by reverse transcription of messenger RNA ("mRNA") lacking intervening sequences (introns).

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator www.ncbi.nlm.nih.gov/BLAST. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The term "ligand," as used herein, refers to any protein or proteins that can interact with a receptor binding domain, thus having a "binding affinity" for such domain. Ligands can be soluble or membrane bound, and they can be a naturally occurring protein, or synthetically or recombinantly produced. The ligand can also be a nonprotein molecule that acts as ligand when it interacts with the receptor binding domain. Interactions between the ligand and receptor binding domain include, but are not limited to, any covalent or non-covalent interactions. The receptor binding domain is any region of the receptor molecule, e.g., Notch, that interacts directly or indirectly with the ligand, e.g., Jagged1. If the Notch-Jagged1 interaction acts as an on-off switch, Jagged1 can provide the receptor binding domain, and Notch or a component produced as a result of the Notch-Jagged1 interaction can act as the ligand.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "oligonucleotide or oligomer", as used herein, refers to a molecule comprised of two or more deoxyribonucleotides or ribonucleotides, preferably more than three. Its exact size will depend on many factors, which in turn depend on the ultimate function or use of the oligonucleotide. An oligonucleotide may be derived synthetically or by cloning.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

A cell that comprises an exogenous nucleic acid is referred to as a "recombinant cell." Such a cell may be a eukaryotic cell or a prokaryotic cell. A gene which is expressed in a recombinant cell wherein the gene comprises a recombinant polynucleotide, produces a "recombinant polypeptide."

By the term "specifically binds," as used herein, is meant a compound, e.g., a protein, a nucleic acid, an antibody, and the like, which recognizes and binds a specific molecule, but does not substantially recognize or bind other molecules in a sample.

By "tag" polypeptide is meant any protein which, when linked by a peptide bond to a protein of interest, may be used to localize the protein, to purify it from a cell extract, to immobilize it for use in binding assays, or to otherwise study its biological properties and/or function. A chimeric (i.e., fusion) protein containing a "tag" epitope can be immobilized on a resin which binds the tag. Such tag epitopes and resins which specifically bind them are well known in the art and include, for example, tag epitopes comprising a plurality of sequential histidine residues (His6), which allows isolation of a chimeric protein comprising such an epitope on nickel-nitrilotriacetic acid-agarose, a hemagglutinin (HA) tag epitope allowing a chimeric protein comprising such an epitope to bind with an anti-HA-monoclonal antibody affinity matrix, a myc tag epitope allowing a chimeric protein comprising such an epitope to bind with an anti-myc-monoclonal antibody affinity matrix, a glutathione-S-transferase tag epitope, and a maltose binding protein (MBP) tag epitope, which can induce binding between a protein comprising such an epitope and a glutathione- or maltose-Sepharose column, respectively. Production of proteins comprising such tag epitopes is well known in the art and is described in standard treatises, such as Sambrook and Russell (2001, Molecular Cloning, A Laboratory Approach, Cold Spring Harbor Press, Cold Spring Harbor, N.Y.), and Ausubel et al. (2002, Current Protocols in Molecular Biology, John Wiley & Sons, NY). Likewise, antibodies to the tag epitope (e.g., anti-HA, anti-myc antibody 9E10, and the like) allow detection and localization of the fusion protein in, for example, Western blots, ELISA assays, and immunostaining of cells.

A "therapeutic protein," as used herein, refers to protein that improves or maintains the health of a cell, a tissue, and/or an organism expressing the protein or that of a cell in proximity to the cell expressing the protein. Numerous exemplary therapeutic proteins are widely-known in the art and are not listed here since they are well-known to the artisan.

A "recombinant cell" is a host cell that comprises a recombinant polynucleotide.

By the term "exogenous nucleic acid" is meant that the nucleic acid has been introduced into a cell or an animal using technology which has been developed for the purpose of facilitating the introduction of a nucleic acid into a cell or an animal.

To "treat" a disease as the term is used herein, means to reduce the frequency of the disease or disorder reducing the frequency with which a symptom of the one or more symptoms disease or disorder is experienced by an animal.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Xenogeneic" refers to a graft derived from an animal of a different species.

Description

Aberrant Notch signaling has been associated with human cancers including acute T-cell lymphoblastic leukemia and cervical cancer, and is strongly implicated in tumorigenesis including mouse mammary tumor formation. The present invention relates to the discovery that activation of Notch 2 signaling in breast cancer cells is a potent suppressor of malignant cell growth, proliferation, survival and tumorigenesis in both in vitro assays and in vivo. Thus, the invention includes compositions and methods related to modulating Notch 2 signaling in breast cancer cells.

Nucleic Acids and Polypeptides

In an embodiment, a composition of the invention comprises a nucleic acid encoding human Notch 2 intracellular domain (hNotch2ICD). Full-length Notch 2 (GenBank accession number NM_024408) is set forth in SEQ ID NO:1. In an aspect, a nucleic acid encoding hNotch2ICD of the invention comprises a nucleic acid sequence encoding the polypeptide comprising amino acid residues 1703-2471 of full length Notch 2 polypeptide, as set forth in SEQ ID NO:2.

In another embodiment, a Notch 2 intracellular domain comprises a mutant, fragment or variant of SEQ ID NO:2. The identification, characterization, and preparation of a mutant, fragment or variant of SEQ ID NO:2 is set forth in detail elsewhere herein. The skilled artisan, when armed with the disclosure set forth herein, will know how to identify a mutant, fragment or variant of SEQ ID NO:2 having the biological activity of hNotch2ICD, as set forth herein.

In yet another embodiment, a Notch 2 intracellular domain comprises a mutant, fragment or variant of SEQ ID NO:1. The identification, characterization, and preparation of a mutant, fragment or variant of SEQ ID NO:1 is set forth in detail elsewhere herein. The skilled artisan, when armed with the disclosure set forth herein, will know how to identify a mutant, fragment or variant of SEQ ID NO:1 having the biological activity of hNotch2ICD, as set forth herein.

In another embodiment, the composition includes a regulatory polynucleotide sequence operably linked to a polynucleotide sequence that encodes Notch 2 expression downstream. In another embodiment, the composition includes a nucleic acid encoding hNotch2ICD covalently linked to a polypeptide tag. In still another embodiment of the invention, the composition includes a nucleic acid encoding hNotch2ICD expressed in a vector.

One skilled in the art will readily appreciate that as a result of the degeneracy of the genetic code, many different nucleotide sequences may encode the same polypeptide. That is, an amino acid may be encoded by one of several different codons, and a person skilled in the art can readily determine that while one particular nucleotide sequence may differ from another, the polynucleotides may in fact encode polypeptides with identical amino acid sequences. As such, polynucleotides that vary due to differences in codon usage are specifically contemplated by the present invention.

In other related aspects, the invention includes an isolated nucleic acid encoding Notch2ICD, that inhibits mammary malignant cell growth, operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

In an embodiment of the invention, the composition includes a nucleic acid encoding hNotch2ICD covalently linked to a polypeptide tag expressed in a vector, the polypeptide comprising amino acids 1703 to 2471 of the hNotch 2 receptor and a polypeptide tag. In another embodiment, a composition includes a nucleic acid encoding a mutant, fragment or variant of SEQ ID NO:2.

The incorporation of a desired polynucleotide into a vector and the choice of vectors is well-known in the art as described in, for example, Sambrook, 2001, Molecular Cloning: A Laboratory Manuel, $3^{rd}$ ed. (Cold Spring Harbor Laboratory Press, Cold Spring Harbor, N.Y.), and Ausubel, ed., 1999, Current Protocols in Molecular Biology (John Wiley & Sons, N.Y.).

The nucleic acid sequence can be cloned into a number of types of vectors. However, the present invention should not be construed to be limited to any particular vector. Instead, the present invention should be construed to encompass a wide plethora of vectors which are readily available and/or well-known in the art. For example, a nucleic acid encoding hNotch2ICD of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector and a eukaryotic vector. However, based on the disclosure set forth herein, the skilled artisan will understand that other vectors may be useful in the present invention. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook, 2001, Molecular Cloning: A Laboratory Manuel, $3^{rd}$ ed. (Cold Spring Harbor Laboratory Press, Cold Spring Harbor, N.Y.), and Ausubel, ed., 1999, Current Protocols in Molecular Biology (John Wiley & Sons, N.Y.), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

Promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202, 5,928,906). Furthermore, it is contemplated the control sequences that direct transcription and/or expression of sequences within non-nuclear organelles such as mitochondria, chloroplasts, and the like, can be employed as well.

It will be understood by the skilled artisan that a promoter and/or enhancer that effectively directs the expression of the DNA segment in the cell type, organelle, and organism can be chosen for expression. One of skill in the art of molecular biology knows how to use promoters, enhancers, and cell type combinations for protein expression. For example, see Sambrook, 2001, Molecular Cloning: A Laboratory Manuel, 3$^{rd}$ ed. (Cold Spring Harbor Laboratory Press, Cold Spring Harbor, N.Y.). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In order to assess the expression of hNotch2ICD in breast cancer cells, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479: 79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of hNotch2ICD polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Polynucleotides of hNotch2ICD may be prepared using a variety of techniques, which are useful for the preparation of specifically desired hNoth2ICD polynucleotides. For example, a polynucleotide may be amplified from a cDNA prepared from a suitable cell or tissue type. Such a polynucleotide may be amplified via polymerase chain reaction (PCR). Using this approach, sequence-specific primers are designed based on the sequences provided herein, and may be purchased or synthesized directly. An amplified portion of the primer may be used to isolate a full-length gene, or a desired portion thereof, from a suitable DNA library using well known techniques. A library (cDNA or genomic) is screened using one or more polynucleotide probes or primers suitable for amplification. Preferably, the library is size-selected to include larger polynucleotide sequences. Random primed libraries may also be preferred in order to identify 5' and other upstream regions of the genes. Genomic libraries are preferred for obtaining introns and extending 5' sequences. The hNotch2ICD polynucleotide contemplated by the present invention may also be selected from a library of cDNA polynucleotide sequences.

For hybridization techniques, a partial polynucleotide sequence may be labeled (e.g., by nick-translation or end-labeling with $^{32}$P) using well known techniques. A bacterial or bacteriophage library may then be screened by hybridization to filters containing denatured bacterial colonies (or lawns containing phage plaques) with the labeled probe (see, e.g., Sambrook et al., Molecular Cloning: A Laboratory Manual, Cold Spring Harbor Laboratories, Cold Spring Harbor, N.Y., 2001). Hybridizing colonies or plaques are selected and expanded, and the DNA is isolated for further analysis.

Alternatively, numerous amplification techniques are known in the art for obtaining a full-length coding sequence from a partial cDNA sequence. Within such techniques, amplification is generally performed via PCR. One such technique is known as "rapid amplification of cDNA ends" or RACE (see, e.g., Sambrook et al., Molecular Cloning: A Laboratory Manual, Cold Spring Harbor Laboratories, Cold Spring Harbor, N.Y., 2001).

Alternatively, hNotch2ICD polynucleotide molecules may be generated by in vitro or in vivo transcription of suitable DNA sequences (e.g., polynucleotide sequences encoding a target polypeptide, or a desired portion thereof), provided that the DNA is incorporated into a vector with a suitable RNA polymerase promoter (such as for example, T7, U6, H1, or SP6 although other promoters may be equally useful.

As such, the invention comprises an hNotch2ICD polynucleotide, such as exemplified in SEQ ID NO: 1. The polynucleotide and polypeptide sequences for various Notch receptors may be found at computerized databases known to those of ordinary skill in the art. One such database is the National Center for Biotechnology Information's Genbank and GenPept databases. The nucleic acid sequences for these known genes may be amplified, combined with the sequences disclosed herein (e.g., ligated) and/or expressed using the techniques disclosed herein or by any technique that would be know to those of ordinary skill in the art (e.g., Sambrook, 2001, Molecular Cloning: A Laboratory Manuel, $3^{rd}$ ed. (Cold Spring Harbor Laboratory Press, Cold Spring Harbor, N.Y.). Though a nucleic acid may be expressed in an in vitro expression system, in preferred embodiments the nucleic acid comprises a vector for in vivo replication and/or expression.

The invention additionally includes an isolated polypeptide encoded by an hNotch2ICD nucleic acid. The amino acid sequence encoded by hNotch2ICD is provided herein in SEQ ID NO:3. As stated above, the invention should in no way be construed to be limited to SEQ ID NO:3. Rather, the invention should be construed to include any hNotch2ICD polypeptide mutant, variant, or fragment thereof, having the biological activity of hNotch2ICD as defined herein.

The present invention also provides for analogs of proteins or peptides encoded by an hNotch2ICD gene. Analogs, as defined herein, can differ from naturally occurring protein or peptides by conservative amino acid sequence differences or by modifications which do not affect sequence, or by both.

In addition to hNotch2ICD peptides, the invention provides for peptides having the biological activity of hNotch2ICD, as defined herein. One skilled in the art would appreciate, based on the sequences disclosed herein, that overlapping fragments of hNotch2ICD can be generated using standard recombinant technology, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York). One skilled in the art would appreciate, based on the disclosure presented herein, that the biological activity of hNotch2ICD fragments could be tested by injecting the material into mice and evaluating whether injected mice demonstrate inhibition of breast tumor growth. Inhibiting of breast tumor growth would serve as an indication that the hNotch2ICD fragment retained biological activity.

As stated above, the present invention also provides for analogs of proteins or peptides encoded by hNotch2ICD. Analogs can differ from naturally occurring proteins or peptides by conservative amino acid sequence differences or by modifications which do not affect sequence, or by both. Any number of procedures may be used for the generation of mutant, derivative or variant forms of hNotch2ICD using recombinant DNA methodology well known in the art such as, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York).

For example, conservative amino acid changes may be made, which although they alter the primary sequence of the protein or peptide, do not normally alter its function. Conservative amino acid substitutions typically include substitutions within the following groups:
glycine, alanine;
valine, isoleucine, leucine;
aspartic acid, glutamic acid;
asparagine, glutamine;
serine, threonine;
lysine, arginine (in positions other than proteolytic enzyme recognition sites);
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

By the term "biological activity of hNotch2ICD" as used herein is meant the ability of a molecule inhibit the growth of a mammalian breast cancer cell, and in particular, a human breast cancer cell. The skilled artisan would further appreciate, based upon the instant disclosure, that the invention is not limited to any particular method of assessing the activity of hNotch2ICD and that the invention encompasses any assay to assess the activity of hNotch2ICD known in the art or to be developed in the future.

Diagnosis and Prognosis

The present invention also includes methods of characterizing and classifying breast cancer tumors by the expression pattern of Notch receptor proteins tumor cells. Cancer cells obtained during routine biopsies are typically assessed by tumor type, size and grade. A prognosis for breast cancer includes these variables as well as lymph node status, degree of vascular invasion of the tumor, estrogen and progesterone receptor status, cell proliferation index, S phase, DNA ploidy and growth factors. Yet it is widely acknowledged that tumor grade, lymph node status and hormone receptor status are the most helpful in formulating a prognosis for any given cancer. It is also widely held that using a combination of factors is the most accurate means of formulating a prognosis.

As described in the present invention, breast cancer cells obtained during routine tumor biopsies can be assayed for relative expression of Notch receptors, especially Notch 2 and Notch 4. Given the correlation of Notch 2 with well-defined tumors and better patient survival and Notch 4 with more invasive tumors and poor patient survival, this prognostic assay would point to specific treatment directions, identifying more aggressive cancers indicative of shorter disease free periods and overall survival. Adding an analysis of Notch receptor expression to the arsenal of breast cancer assessment permits the development of a personalized treatment plan for each patient based upon not only cancer stage but also cancer type. The present invention thereby includes diagnostic/prognostic methods of use and kits.

Accordingly, the invention also includes a method of identifying a cell having a Notch 2-related mammary adenocarcinoma, based on characterization of the Notch 2 signaling in a breast cancer cell, and using a Notch2ICD as set forth elsewhere herein.

Detection

In an embodiment, a diagnostic method of the invention comprises collecting a sample from a patient, contacting the sample with at least one antibody specific for Notch 2, and detecting antibody binding thereto. The relative amounts of Notch 2 expressed in the sample are useful in formulating a prognosis and treatment plan.

Any methods available in the art, or yet to be discovered, for identification or detection of Notch 2 are encompassed herein. In the present invention, Notch 2 can be detected at a nucleic acid level or a protein level. In order to determine whether the levels of Notch 2 measured in the sample are indicative of poor prognosis for breast cancer, Notch 2 expression levels are measured in the body sample to be examined and compared with a corresponding body sample that originates from a normal, cancer-free individual. In another embodiment of the invention, prognosis is determined by measuring levels of Notch 2 in the body sample to be examined and comparing with an average value obtained from more than one normal, cancer-free individuals. In still another embodiment of the invention, relative levels of Notch 2 are determined by measuring levels of Notch 2 in the body sample to be examined and comparing with levels obtained from a body sample obtained from the same individual from a cancer free tissue or at a different time, Methods for detecting Notch 2 include any method that determines the quantity or the presence of the biomarkers either at the nucleic acid or protein level. Such methods are well known in the art and include, but are not limited to, Western blots, Northern blots, Southern blots, ELISA, immunoprecipitation, immunofluorescence, flow cytometry, immunocytochemistry, nucleic acid hybridization techniques, nucleic acid reverse transcription methods, and nucleic acid amplification methods. In an embodiment, Notch 2 is detected on a protein level using, for example, antibodies that are directed against Notch 2, or fragments thereof. Such antibodies can be used in various methods such as Western blot, ELISA, immunoprecipitation, or immunocytochemistry techniques, among others.

The invention should not be limited to any one method of protein or nucleic acid detection method recited herein, but rather should encompass all known or heretofore unknown methods of detection as are, or become, known in the art.

In one embodiment, antibodies specific for Notch 2 proteins are used to detect the relative expression of these proteins in a body sample. The method comprises obtaining a tissue sample from a patient, contacting the tissue sample with at least one antibody directed to Notch 2, to determine relative levels of expression. One of skill in the art will recognize that the immunocytochemistry method described herein below is performed either manually or in an automated fashion.

When the antibody used in the methods of the invention is a polyclonal antibody (IgG), the antibody is generated by inoculating a suitable animal with a Notch 2 protein, peptide or a fragment thereof. Antibodies produced in the inoculated animal which specifically bind the Notch 2 protein are then isolated from fluid obtained from the animal. Notch 2 antibodies may be generated in this manner in several non-human mammals such as, but not limited to goat, sheep, horse, rabbit, and donkey. Methods for generating polyclonal antibodies are well known in the art and are described, for example in Harlow, et al. (1988, In: Antibodies, A Laboratory Manual, Cold Spring Harbor, N.Y.). These methods are not repeated herein as they are commonly used in the art of antibody technology.

When the antibody used in the methods of the invention is a monoclonal antibody, the antibody is generated using any well known monoclonal antibody preparation procedures such as those described, for example, in Harlow et al. (supra) and in Tuszynski et al. (1988, Blood, 72:109-115). Given that these methods are well known in the art, they are not replicated herein. Generally, monoclonal antibodies directed against a desired antigen are generated from mice immunized with the antigen using standard procedures as referenced herein. Monoclonal antibodies directed against full length or peptide fragments of biomarker may be prepared using the techniques described in Harlow, et al. (supra).

Samples may need to be modified in order to render the antigens accessible to antibody binding. In a particular aspect of the immunocytochemistry methods, slides are transferred to a pretreatment buffer, for example phosphate buffered saline containing Triton-X. Incubating the sample in the pretreatment buffer rapidly disrupts the lipid bilayer of the cells and renders the antigens (i.e., Notch 2 proteins) more accessible for antibody binding. The pretreatment buffer may comprise a polymer, a detergent, or a nonionic or anionic surfactant such as, for example, an ethyloxylated anionic or nonionic surfactant, an alkanoate or an alkoxylate or even blends of these surfactants or even the use of a bile salt. The pretreatment buffers of the invention are used in methods for making antigens more accessible for antibody binding in an immunoassay, such as, for example, an immunocytochemistry method or an immunohistochemistry method.

Any method for making antigens more accessible for antibody binding may be used in the practice of the invention, including antigen retrieval methods known in the art. See, for example, Bibbo, 2002, Acta. Cytol. 46:25 29; Saqi, 2003, Diagn. Cytopathol. 27:365 370; Bibbo, 2003, Anal. Quant. Cytol. Histol. 25:8 11. In some embodiments, antigen retrieval comprises storing the slides in 95% ethanol for at least 24 hours, immersing the slides one time in Target Retrieval Solution pH 6.0 (DAKO S1699)/dH2O bath preheated to 95° C., and placing the slides in a steamer for 25 minutes.

Following pretreatment or antigen retrieval to increase antigen accessibility, samples are blocked using an appropriate blocking agent, e.g., a peroxidase blocking reagent such as hydrogen peroxide. In some embodiments, the samples are blocked using a protein blocking reagent to prevent non-specific binding of the antibody. The protein blocking reagent may comprise, for example, purified casein, serum or solution of milk proteins. An antibody directed to a biomarker of interest is then incubated with the sample.

Techniques for detecting antibody binding are well known in the art. Antibody binding to a protein of interest may be detected through the use of chemical reagents that generate a detectable signal that corresponds to the level of antibody binding and, accordingly, to the level of Notch 2 protein expression. In one of the preferred immunocytochemistry methods of the invention, antibody binding is detected through the use of a secondary antibody that is conjugated to a labeled polymer. Examples of labeled polymers include but are not limited to polymer-enzyme conjugates. The enzymes in these complexes are typically used to catalyze the deposition of a chromogen at the antigen-antibody binding site, thereby resulting in cell staining that corresponds to expression level of the protein of interest. Enzymes of particular interest include horseradish peroxidase (HRP) and alkaline phosphatase (AP). Commercial antibody detection systems, such as, for example the Dako Envision+system (Dako North America, Inc., Carpinteria, Calif.) and Mach 3 system (Biocare Medical, Walnut Creek, Calif.), may be used to practice the present invention.

In one particular immunocytochemistry method of the invention, antibody binding to Notch 2 and/or Notch4 is detected through the use of an HRP-labeled polymer that is conjugated to a secondary antibody. Antibody binding can also be detected through the use of a mouse probe reagent, which binds to mouse monoclonal antibodies, and a polymer conjugated to HRP, which binds to the mouse probe reagent. Slides are stained for antibody binding using the chromogen 3,3-diaminobenzidine (DAB) and then counterstained with hematoxylin and, optionally, a bluing agent such as ammonium hydroxide or TBS/Tween-20. In some aspects of the invention, slides are reviewed microscopically by a cytotechnologist and/or a pathologist to assess cell staining (i.e., biomarker overexpression). Alternatively, samples may be reviewed via automated microscopy or by personnel with the assistance of computer software that facilitates the identification of positive staining cells.

Detection of antibody binding can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

In regard to detection of antibody staining in the immunocytochemistry methods of the invention, there also exist in the art video-microscopy and software methods for the quantitative determination of an amount of multiple molecular species (e.g., various Notch 2 proteins) in a biological sample, wherein each molecular species present is indicated by a representative dye marker having a specific color. Such methods are also known in the art as calorimetric analysis methods. In these methods, video-microscopy is used to provide an image of the biological sample after it has been stained to visually indicate the presence of a particular biomarker of interest. Some of these methods, such as those disclosed in U.S. patent application Ser. No. 09/957,446 and U.S. patent application Ser. No. 10/057,729 to Marcelpoil, incorporated herein by reference, disclose the use of an imaging system and associated software to determine the relative amounts of each molecular species present based on the presence of representative color dye markers as indicated by those color dye markers' optical density or transmittance value, respectively, as determined by an imaging system and associated software. These techniques provide quantitative determinations of the relative amounts of each molecular species in a stained biological sample using a single video image that is "deconstructed" into its component color parts.

The antibodies used to practice the invention are selected to have high specificity for the proteins of interest. Methods for making antibodies and for selecting appropriate antibodies are known in the art. See, for example, Celis, J. E. ed. (in press) Cell Biology & Laboratory Handbook, 3rd edition (Academic Press, New York), which is herein incorporated in its entirety by reference. In some embodiments, commercial antibodies directed to specific Notch 2 proteins may be used to practice the invention. The antibodies of the invention may be selected on the basis of desirable staining of cytological, rather than histological, samples. That is, in particular embodiments the antibodies are selected with the end sample type (i.e., cytology preparations) in mind and for binding specificity.

One of skill in the art will recognize that optimization of antibody titer and detection chemistry is needed to maximize the signal to noise ratio for a particular antibody. Antibody concentrations that maximize specific binding to the biomarkers of the invention and minimize non-specific binding (or "background") will be determined in reference to the type of biological sample being tested. In particular embodiments, appropriate antibody titers for use cytology preparations are determined by initially testing various antibody dilutions on formalin-fixed paraffin-embedded normal tissue samples. Optimal antibody concentrations and detection chemistry conditions are first determined for formalin-fixed paraffin-embedded tissue samples. The design of assays to optimize antibody titer and detection conditions is standard and well within the routine capabilities of those of ordinary skill in the art. After the optimal conditions for fixed tissue samples are determined, each antibody is then used in cytology preparations under the same conditions. Some antibodies require additional optimization to reduce background staining and/or to increase specificity and sensitivity of staining in the cytology samples.

Furthermore, one of skill in the art will recognize that the concentration of a particular antibody used to practice the methods of the invention will vary depending on such factors as time for binding, level of specificity of the antibody for the protein, and method of tissue sample preparation. Moreover, when multiple antibodies are used, the required concentration may be affected by the order in which the antibodies are applied to the sample, i.e., simultaneously as a cocktail or sequentially as individual antibody reagents. Furthermore, the detection chemistry used to visualize antibody binding to a biomarker of interest must also be optimized to produce the desired signal to noise ratio.

Immunoassays

Immunoassays, in their simplest and most direct sense, are binding assays. Certain preferred immunoassays are the various types of enzyme linked immunosorbent assays (ELISA) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, antibodies binding to the biomarker proteins of the invention are immobilized onto a selected surface exhibiting protein affinity, such as a well in a polystyrene microtiter plate. Then, a test composition suspected of containing the biomarker antigen, such as a clinical sample, is added to the wells. After binding and washing to remove non-specifically bound immunecomplexes, the bound antibody may be detected. Detection is generally achieved by the addition of a second antibody specific for the target protein, that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the biomarker antigen are immobilized onto the well surface and then contacted with the antibodies of the invention. After binding and washing to remove non-specifically bound immunecomplexes, the bound antigen is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the proteins or peptides are immobilized, involves the use of antibody competition in the detection. In this ELISA, labeled antibodies are added to the wells, allowed to bind to the Notch 2 protein, and detected by means of its label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immunecomplexes. These are described as follows:

In coating a plate with either antigen or antibody, the wells of the plate are incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating of nonspecific adsorption sites on the immobilizing surface reduces the background caused by nonspecific binding of antisera to the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control and/or clinical or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

"Under conditions effective to allow immunecomplex (antigen/antibody) formation" means that the conditions preferably include diluting the antigens and antibodies with solutions such as, but not limited to, BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this label is an enzyme that generates a color or other detectable signal upon incubating with an appropriate chromogenic or other substrate. Thus, for example, the first or second immunecomplex can be detected with a urease, glucose oxidase, alkaline phosphatase or hydrogen peroxidase-conjugated antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

Nucleic Acid-Based Techniques

In another embodiment, the expression of Notch 2 is detected at the nucleic acid level. Nucleic acid-based techniques for assessing expression are well known in the art and include, for example, determining the level of Notch 2 and/or Notch 4 mRNA in a body sample. Many expression detection methods use isolated RNA. Any RNA isolation technique that does not select against the isolation of mRNA can be utilized for the purification of RNA from body samples (see, e.g., Ausubel, ed., 1999, Current Protocols in Molecular Biology (John Wiley & Sons, New York). Additionally, large numbers of tissue samples can readily be processed using techniques well known to those of skill in the art, such as, for example, the single-step RNA isolation process of Chomczynski, 1989, U.S. Pat. No. 4,843,155).

The term "probe" refers to any molecule that is capable of selectively binding to a specifically intended target biomolecule, for example, a nucleotide transcript or a protein encoded by or corresponding to a biomarker. Probes can be synthesized by one of skill in the art, or derived from appropriate biological preparations. Probes may be specifically designed to be labeled with a detectable label. Examples of molecules that can be used as probes include, but are not limited to, RNA, DNA, proteins, antibodies, and organic molecules.

Isolated mRNA as a biomarker can be detected in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker of the present invention. Hybridization of an mRNA with the probe indicates that the biomarker in question is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array (Santa Clara, Calif.). A skilled artisan can readily adapt known mRNA detection methods for use in detecting the level of mRNA encoded by the biomarkers of the present invention.

An alternative method for determining the level of biomarker mRNA in a sample involves the process of nucleic acid amplification, e.g., by RT-PCR (the experimental embodiment set forth in Mullis, 1987, U.S. Pat. No. 4,683,202), ligase chain reaction (Barany, 1991, Proc. Natl. Acad. Sci. USA, 88:189 193), self sustained sequence replication (Guatelli, 1990, Proc. Natl. Acad. Sci. USA, 87:1874 1878), transcriptional amplification system (Kwoh, 1989, Proc. Natl. Acad. Sci. USA, 86:1173 1177), Q-Beta Replicase (Lizardi, 1988, Bio/Technology, 6:1197), rolling circle replication (Lizardi, U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, biomarker expression is assessed by quantitative fluorogenic RT-PCR (i.e., the TaqMan.RTM. System). Such methods typically use pairs of oligonucleotide primers that are specific for the biomarker of interest. Methods for designing oligonucleotide primers specific for a known sequence are well known in the art.

Biomarker expression levels of RNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of biomarker expression may also comprise using nucleic acid probes in solution.

Therapeutic Applications

The present invention also includes the inhibition (or "suppression") of breast tissue malignancies by activation of the Notch 2 signaling pathway. In an aspect, breast tissue malignancies that can benefit by an increase in constitutively active hNotch2ICD can be ameliorated by administering constitutively active exogenous hNotch2ICD or enhancing the endogenous expression of hNotch2ICD in breast cancer cells.

However, it will also be understood, based on the disclosure set forth herein, that the present invention encompasses treatment of other types of cancer, wherein such cancers are associated with the Notch 2 signaling pathway. In particular, the invention includes inhibition or treatment of other types of cancer that can benefit from activation of the Notch 2 signaling pathway.

Notch signaling is also implicated in various types of cancer including, but not limited to, lymphoma, pancreatic cancer, medulloblastoma, skin cancer, and Kaposi's sarcoma. See, e.g., Massi et al. (Modern Pathology, 2006, 19:246-254) and Curry et al. (Mol. Cancer Ther., 2007, 6:1983-1992). Accordingly, other cancers involving a downregulation of Notch 2 signaling, Notch 2 expression, Notch 2 levels, or Notch 2 activity will be understood, according to the present invention, to be treatable according to the present invention. This is because it has been shown herein for the first time that tissue malignancies that can benefit by an increase in constitutively active hNotch2ICD can be ameliorated by administering constitutively active exogenous hNotch2ICD or enhancing the endogenous expression of hNotch2ICD.

The invention also includes a method of administering constitutively active exogenous hNotch2ICD to a patient with breast cancer wherein the composition is incorporated into breast cancer cells and suppresses their growth. In another embodiment, the invention includes a method of enhancing endogenous expression of constitutively active Notch 2 in breast cancer cells, where those cancer cells are in a patient. In an aspect, a patient is a human patient.

In another embodiment, the invention includes a method of administering constitutively active exogenous mutant, fragment or variant of hNotch2ICD to a patient with breast cancer wherein the composition is incorporated into breast cancer cells and suppresses their growth. In another embodiment, the invention includes a method of enhancing endogenous expression of constitutively active mutant, fragment or variant of Notch 2 in breast cancer cells, where those cancer cells are in a patient. The identification, preparation and characterization of a mutant, fragment, or variant of hNotch2ICD is set forth in detail elsewhere herein. In an aspect, a patient is a human patient.

Pharmaceutical Compositions

The present invention includes methods and compositions for treating a disease, i.e. breast cancer and the like, in a mammal by the administration of therapeutic agent, e.g. hNotch2ICD. Administration of the therapeutic agent in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art Administration of hNotch2ICD may be accomplished through the administration of the nucleic acid molecule encoding hNotch2ICD, or through the administration of a hNotch2ICD polypeptide (see, for example, Felgner et al., U.S. Pat. No. 5,580,859, Pardoll et al. 1995; Stevenson et al. 1995; Molling 1997; Donnelly et al. 1995; Yang et al. II; Abdallah et al. 1995). Pharmaceutical formulations, dosages and routes of administration for nucleic acids are generally disclosed, for example, in Felgner et al., supra.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including by direct injection into the diseased tissue. For example, the therapeutic agent may be directly injected into the tumor. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for administration directly to a tumor (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The expression vectors, transduced cells, polynucleotides and polypeptides (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.); lipid A, trehalose dimycolate and dimethyldioctadecylammonium bromide (DDA), Freund's adjuvant, and IL-12. Other components may include a polyoxypropylene-polyoxyethylene block polymer (PLURONIC), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

The active ingredients of the present invention can be provided in unit dosage form wherein each dosage unit contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

Gene Therapy Administration

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome, aggregated protein or transporter molecule.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

Cells containing the therapeutic agent may also contain a suicide gene i.e., a gene which encodes a product that can be used to destroy the cell. In many gene therapy situations, it is desirable to be able to express a gene for therapeutic purposes in a host, cell but also to have the capacity to destroy the host cell at will. The therapeutic agent can be linked to a suicide gene, whose expression is not activated in the absence of an activator compound. When death of the cell in which both the agent and the suicide gene have been introduced is desired, the activator compound is administered to the cell thereby activating expression of the suicide gene and killing the cell. Examples of suicide gene/prodrug combinations which may be used are herpes simplex virus-thymidine kinase (HSV-tk) and ganciclovir, acyclovir; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

These methods described herein are by no means all-inclusive, and further methods to suit the specific application will be apparent to the ordinary skilled artisan. Moreover, the effective amount of the compositions can be further approximated through analogy to compounds known to exert the desired effect.

Kits

The present invention includes a kit for activating the Notch 2 signaling pathway in breast cancer cells. The kit comprises an effective amount of a soluble Notch2ICD, an applicator, and instructional material for the use of the kit, and the kit is used pursuant to methods disclosed elsewhere herein. In one embodiment, a kit is provided for increasing Notch 2 (e.g., hNotch2ICD) signaling in breast cancer cells in vivo. In one aspect, the soluble component is exogenous Notch2ICD polypeptide. In another aspect, the soluble component is a vector containing a nucleic acid sequence that encodes hNotch2ICD.

In another embodiment of the invention, a kit is provided for amplifying endogenous activation of the Notch 2 signaling pathway expressed by breast cancer cells. In one aspect, the kit comprises a drug or pharmaceutical agent that can activated Notch 2 signaling. In another aspect, the kit comprises a nucleic acid that encodes hNotch 2CD. As will be understood by one of skill in the art when armed with the disclosure set forth herein, a kit of the present invention may be used for modulation of any process or activity related to the amplifying Notch 2 signaling in breast cancer cells.

The invention further includes various kits which comprise a polypeptide of the invention, and/or a nucleic acid encoding the polypeptide, an applicator, and instructional materials which describe use of the kit to perform the methods of the invention. Although exemplary kits are described below, the contents of other useful kits will be apparent to the skilled artisan in light of the present disclosure. Each of these kits is included within the invention.

In one aspect, the invention includes a kit for activating Notch 2 signaling in breast cancer cells. The kit is used pursuant to the methods disclosed in the invention. Briefly, the kit may be used to administer a soluble pharmaceutical agent that activates the endogenous Notch 2 signaling pathway in breast cancer cells, and which suppresses the growth, proliferation and/or survival of the cancer cell. As demonstrated elsewhere herein, transfecting a cancer cell with an effective amount of Notch 2, and any combination thereof, mediates a plethora of effects as disclosed herein. These effects include, but are not limited to, the suppression of the cancer cell's growth, proliferation and survival. Thus, the kit comprises an effective amount of at least one form of constitutively active Notch 2. The kit further comprises an applicator and an instructional material for the use of the kit.

The particular applicator included in the kit will depend on, e.g., the method used to administer the protein, and/or nucleic acid encoding the same, as well as the animal or cell to which the protein and/or nucleic acid of the invention is to be administered, and such applicators are well-known in the art and may include, among other things, a pipette, a syringe, a dropper, and the like. Moreover, the kit comprises an instructional material for the use of the kit. These instructions simply embody the disclosure provided herein.

The kit can include a pharmaceutically-acceptable carrier. The composition is provided in an appropriate effective amount as set forth elsewhere herein. Further, the route of administration and the frequency of administration are as previously set forth elsewhere herein.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

The invention is now described with reference to the following Examples. These Examples are provided for the purpose of illustration only, and the invention is not limited to these Examples, but rather encompasses all variations which are evident as a result of the teachings provided herein.

The experiments disclosed herein demonstrate the role of Notch 2 signaling as a potent suppressor of breast cancer cell growth, proliferation and survival. The concept of exploiting Notch 2 signaling to inhibit breast cancer growth and proliferation is a novel method in the treatment of this disease.

DNA Constructs

Constructs for Notch 2 and Notch4 intracellular domain sequences were utilized as eukaryotic expression vectors in pcDNA vectors. The human (h) Notch2ICD encodes for amino acids 1703-2471, contains the V5 epitope tag, and has been extensively characterized (Small et al., 2003, J. Biol. Chem. 278:16405-16413; Small et al., 2001, J. Biol. Chem. 276:32033-32030). The mouse (m) Notch4ICD (int3) cDNA was originally obtained from J. Kitajewski. This mNotch4ICD was cloned into the SalI site of pcDNA3.1 and encodes from amino acid 1410 to amino acid 1958 with an HA epitope tag. Empty vectors were used for transfections to obtain control cell populations. The CBF-1 luciferase construct contains 6 repeats of the CBF-1 binding sequence, and it and the Hrt1 (a generous gift of Eric Olson) promoter luciferase constructs were co-transfected with *Renilla* as a control as described IN O'Neill et al. ((2007) Am. J. Pathol., 171:1023-1036), the entirety of which is incorporated herein by reference.

Cell Culture

MDA-MB-231, a well characterized human mammary adenocarcinoma cell line, was obtained from ATCC (HTB-26), and grown in Earle's αMEM with glutamine and nucleosides (Cellgro) supplemented with 10% fetal bovine serum, 1% nonessential amino acids (Gibco), and 50 µg/ml gentamicin reagent solution (Gibco). At confluence, cells were subcultured at a 1:4 ratio. Cells were stably transfected with expression vectors using GeneJuice (Novagen), and selected with the appropriate resistance antibiotic (200 µg/ml Zeocin or 200 µg/ml hygromycin, both from Invitrogen). All experiments were performed using at least three stable cell populations from individual transfections. For adeoviral transductions, cells were transduced in serum-free medium with 200 pfu/cell for 1 hour, using a LacZ of GFP viral construct as a control. For growth curves, cells were plated in complete medium at a concentration of 15,000-30,000 cells/cm$^2$ in 24 well plates, and counted on day one and then every other day after plating using a Coulter counter. Growth curves were performed with each group measured in quadruplicate, with two counts performed in each well. For assessment of proliferation, cells were incubated in 10 mM bromodeoxyuridine (BrdU) for 4 hrs before fixation in 4% paraformaldehyde and immunostaining. Data shown are representative collected from a minimum of three independent repeats of each experiment. For clonal growth experiments, cells were plated by serial dilution at 100 and 50 cells/well in a 6-well plate. Two weeks later, cells were washed two times with PBS, fixed with methanol, and stained for 10 minutes with toluidine blue (Sigma). Using Scion Image analysis software, a picture of each individual well was taken, and a number of colonies counted and total area covered by colonies calculated.

Statistical analysis was performed by Student's t-test or ANOVA, as appropriate, and differences were considered statistically significant with p<0.05. For soft agar assays, a layer of 4 ml of 0.8% low melting temperature (LMT) agarose (SeaKem) dissolved in MDA-MB-231 growth medium was put into 60 mm dishes and then overlaid with a suspension of cells in 6 ml 0.4% LMT agarose. After 21 days, the dishes were stained with 0.1 mg/ml of p-iodonitrotetrazolium (Sigma) in PBS overnight. The next day, the colonies were counted using a dissecting microscope and pictures taken with a Zeiss AxioCam camera. Other human breast cancer cell lines were obtained from ATCC and grown according to manufacturer's specifications.

Immunoblotting

Cells were lysed with HTNG (20 mM HEPES pH=7.4, 150 mM NaCl, 10% glycerol, 1% Triton X-100, 1.5 mM MgCl$_2$, 1 mM EDTA, protease inhibitor cocktail (Roche), 200 µM NaVO$_4$, 1 mM NaF, 5 mM β-glycerol phosphate) and cleared of insoluble material by centrifugation for 10 minutes at 14,000 rpm at 4° C. Protein concentration was determined by the BCA method, and 50 µg protein loaded per lane. Lysates were subjected to SDS-PAGE followed by electrophoretic transfer to nitrocellulose membrane and immunoblotted with the following antibodies: anti-Notch1 (1 µg/ml), anti-Notch 2 (1 µg/ml, anti-Notch4 (0.4 µg/ml) and anti-Jagged (0.2 µg/ml), all from Santa Cruz, followed by HRP-conjugated secondary antibodies. Bound antibodies were visualized by chemiluminescence (Amersham).

RT-PCR

Total RNA was isolated using TRI Reagent (Sigma) following the manufacturer's protocol. RNA was reverse transcribed using random hexamers in the presence of AMV reverse transcriptase (Promega) to make cDNA. Successful cDNA production was verified using primers against GAPDH of b-actin. Real-time PCR was performed using SYBR green for HES1, Hrt1, and β-actin as the housekeeping gene. cDNA concentration in the samples was adjusted to 50 ng/µl based on the β-actin cDNA content. cDNA (1 µl) and specific primers were added to the SYBR green PCR master mix (Qiagen) and amplification was performed in a Bio-Rad iCycler machine. The forward primer used for Notch 2 was 5'-CACAGAGGCTGGGAAAGGATGATA-3' (SEQ ID NO:4) and the reverse primer used for Notch 2 was 5'-GGC-CACCTGAAGGGAAGCACATA-3' (SEQ ID NO:5).

Immunostaining

BrdU immunostaining was performed using a monoclonal anti-BrdU antibody (MP Biomedicals). Following fixation, cells were treated with 0.3% H$_2$O$_2$ in methanol at room temperature for 20 minutes, followed by treatment with 20 µg/ml proteinase K in 50 mM Tris/5 mM EDTA for 7 minutes at room temperature. Immediately following proteinase K treatment, cells were washed in 0.4% glycerine/PBS and then incubated in 1.5N HCl for 15 minutes at 37° C. Cells were then washed in 0.1M borax buffer, and immunostained with a 1:100 dilution of anti-BrdU, followed by a biotinylated anti-mouse antibody, and the ABC Elite reagent. The antigen was detected by using diaminobenzidine as the chromogen. Ten random fields of cells were captured for each sample, and the percentage BrdU-labeled cells determined by counts of labeled/total cells in a blinded manner. Tumor sections were labeled with biotin dUTP using terminal deoxynucleotide transferase (TdT) to detect DNA fragmentation. Following 3% H$_2$O$_2$ treatment and proteinase K antigen retrieval, tumors were incubated for 1 hour at 37° C. in TdT reaction solution (TdT 0.25 units/µl, Biotin-dUTP 0.4 nmol/ml in TdT Buffer[30 mM Tris-base pH=7.2, 140 mM sodium cacodylate, 1 mM cobalt chloride]). Incubation in TdT Reaction Termination Buffer (300 mM NaCl, 30 mM sodium citrate) quenched TdT activity. Antigen was detected using the ABC Elite Reagent and diaminobenzidine as the chromogen. Quantitation was conducted as described for BrdU immunostaining. Immunostaining for endothelial cells was performed with both anti-PECAM antibodies and the anti-endothelial antigen MECA-32 (both from BD Biosciences) with similar results. For anti-PECAM staining, staining was performed with a biotinyltyramide amplification reagent (Perkin Elmer), using diaminobenzidine as the chromogen. Immunostaining with anti-mouse MECA-32 and LYVE-1 (R & D Systems) was performed as described above for the V5 epitope.

Tumor Specific Markers Levels and Vascularization

Tumor cells release an increased amount of certain factors (hereinafter "tumor specific markers") than their normal counterparts. For example, plasminogen activator (PA) is released from human glioma at a higher level than from normal brain cells (see, e.g., Gullino, pp. 178-184 "Angiogenesis, tumor vascularization, and potential interference with tumor growth" in Mihich (ed. 1985) Biological Responses in Cancer Plenum. Similarly, tumor angiogenesis factor (TAF) is released at a higher level in tumor cells than their normal counterparts. See, e.g., Folkman (1992) Sem. Cancer Biol. 3:89-96.

Various techniques which measure the release of these factors are described in Freshney (1994). Also, see, Unkeless, et al. (1974) J. Biol. Chem. 249:4295-4305; Strickland and Beers (1976) J. Biol. Chem. 251:5694-5702; Whur, et al. (1980) Br. J. Cancer 42:305-312; Gullino, pp. 178-184

"Angiogenesis, tumor vascularization, and potential interference with tumor growth" in Mihich (ed. 1985) Biological Responses in Cancer Plenum; and Freshney (1985) Anticancer Res. 5:111-130.

The ability of tumors to recruit vascular growth is a significant factor when formulating a breast cancer prognosis. The present invention quantified blood endothelial cells by immunohistochemical staining with antisera directed against PECAM and MECA-2 and lymphatic endothelial cells by immunohistochemical staining with an antiserum directed against LYVE-1.

The current invention discloses several cytokine gene targets potentially important for blood and lymph vessel recruitment by tumors that are targets of Notch signaling in breast cancer. Specifically, mNotch4ICD tumors selectively expressed VEGF-C, VEGF-D and placental growth factor (P1GF) but did not express detectable levels of FGF-1. hNotch2ICD tumors had lower levels of angiopoietin-1 (Ang-1), NRP-1 and NRP-2 compared to either control or mNotch4ICD tumors. Additionally, host specific transcripts of VEGFR3 and NRP-1 were detected using mouse primers in both hNotch2ICD and mNotch4ICD tumors but not control tumors.

Tumor Growth In Vivo

Effects of Notch 2 signaling on breast cancer cell growth can be tested in transgenic or immune-suppressed mice. Knock-out transgenic mice can be made, in which a breast cancer gene is disrupted or in which a breast cancer gene is inserted. Knock-out transgenic mice can be made by insertion of a marker gene or other heterologous gene into the endogenous breast cancer gene site in the mouse genome via homologous recombination. Such mice can also be made by substituting the endogenous breast cancer gene with a mutated version of the breast cancer gene, or by mutating the endogenous breast cancer gene, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. By breeding the chimeric mice it is possible to obtain a new line of mice containing the introduced genetic lesion. See, e.g., Capecchi, et al. (1989) Science 244:1288-1292. Chimeric targeted mice can be derived according to Hogan, et al. (1988) Manipulating the Mouse Embryo: A Laboratory Manual CSH Press; and Robertson (ed. 1987) Teratocarcinomas and Embryonic Stem Cells: A Practical Approach IRL Press, Washington, D.C.

Alternatively, various immune-suppressed or immune-deficient host animals can be used. For example, genetically athymic "nude" mouse (see, e.g., Giovanella, et al. (1974) J. Nat'l Cancer Inst. 52:921-930), a SCID mouse, a thymectomized mouse, or an irradiated mouse (see, e.g., Bradley, et al. (1978) Br. J. Cancer 38:263-272; Selby, et al. (1980) Br. J. Cancer 41:52-61) can be used as a host. Transplantable tumor cells (typically about $10^6$ cells) injected into isogenic hosts will produce invasive tumors in a high proportions of cases, while normal cells of similar origin will not.

In one embodiment of the invention, NCr homozygous nude mice (Tactonic) were injected with MDA-MB-231 cells expressing a constitutively active Notch2ICD, Notch4ICD or empty vector either subcutaneously or into the mammary fat pad. After a suitable length of time, preferably 4-8 weeks, tumor growth is measured (e.g., by volume or by its two largest dimensions) and compared to the control. Tumors that have statistically significant reduction (using, e.g., Student's T test) are said to have inhibited growth. In one embodiment, the present invention comprises a method of impeding the growth of cancer cells in vitro.

Tumor Xenograft Growth In Vivo

All protocols involving mice were evaluated and approved by the Maine Medical Center Institutional Animal Care and Use Committee and performed under veterinary supervision. NCr homozygous nude mice (Taconic) at 5-6 weeks of age were injected subcutaneously in the right flank with $2.5 \times 10^6$ stably transfected MDA-MB-231 populations. For the mammary fat pad model, $4.0 \times 10^6$ stably transfected MDA-MB-231 populations were injected into the mammary fat pad with Matrigel (Sigma). Tumor growth was monitored by palpation, and the onset noted when tumors were palpable. Tumor size was measured with calipers, and tumor volume calculated assuming the shape as ellipsoid. Representative data were obtained from 5 mice/experimental group, and the entire experiment was repeated in three independent trials. Prior to collection, moce were injected intraperitoneally with 200 μl of 80 mM BrdU solution at 15 hours and 1 hour prior to collection. Individual tumors were split for fixation in 4% paraformaldehyde and flash freezing in liquid nitrogen, then used for histology and immunostaining, or RNA and protein collection, respectively.

ELISA

Detection of human angiogenic actors in cells and mice with MDA-MB-231 tumors was performed using the Trans-Signal Agiogenesis Antibody Array (Panomics) following the manufacturer's instructions. MDA-MB-231 cells were cultured for 24 hours in serum-free medium. The medium was collected, filtered to remove cellular debris, and 2 ml undiluted media immediately used for the assay. For comparison of secreted angiogenesis factors from tumors, blood was collected from mice by retro-orbital bleed into EDTA-coated microcontainers (Becton Dickenson), plasma separated by centrifugation at 7000×g for 10 minutes, and samples stored at −20° C. until use.

Experimental Example 1

Notch Receptors are Expressed in Various Human Breast Cancer Cell Lines

In order to develop a model of human breast cancer, several well-characterized breast cancer cell lines with tumorgenic phenotype were assessed for Notch expression.

Initial studies evaluated human breast tumor cell lines compared to the MCF10A line, which is a mammary gland-derived, non-tumorigenic line. Several well-characterized breast cancer lines were analyzed for Notch expression, including MCF-7, MDA-MB-231, ZR75-1, MDA-MB-468, and BT474 (FIG. 1A). With the exception of the MCF10A cells, all the human breast cell lines demonstrate a tumorigenic phenotype. Notch 1 protein was detected in all lines except Bt474 and lower levels of Notch 2 were founding all lines except MCF-7. Notch 4 was also widely expressed in the MCF10A, MDA-MB-231 and MDA-MB-468 lines. The cell line MDA-MB-231 line was used for the remainder of the studies disclosed herein since it expressed all of the receptors and ligands tested; thus activation of the Notch signaling pathway in this cell line is overexpression, rather than ectopic expression. Further, this line is amenable to in vitro manipulation and grows successfully as a xenograft in vivo (Anderson, 1984, J. Submicrosc. Cytol. 16:673-690; Fraker, 1984, Cancer Res. 44:5757-5763). The MAD-MB-231 line has been used to study the role of other signaling pathways such as TGFβ-related signals (Sun, 1997, J. Biol. CHem. 272: 25367-25372), and xenografts can be grown in multiple sites, including in bone to address the effect microenvironment plays on metastasis (van der Pluijim, 2001, Am. J. Phathol. 159:971-982).

Experimental Example 2 hNotch2ICD Suppresses, Whereas mNotch4ICD Enhances Breast Cancer Cell Growth and Survival In Vitro In order to determine the differential effects of Notch 2 and Notch 4 signaling on breast cancer cell growth in vitro, several reporter methods of evaluating Notch signaling efficacy were used: (1) CBF-1 reporter transactivation; (2) real time PCR analysis of Notch transcriptional targets HES1 and HRT1 and (3) HES1 promoter reporter.

Activities of endogenous Notch signaling and the NotchICD were evaluated using a CBF-1 response element as a reporter of Notch signaling (FIG. 1B). CBF-1 reporter transactivation in control MDA-MB-231 cells was significant, which was expected since there are ligands/receptors expressed in these cells. However, the endogenous signaling level was very low, and could be significantly activated with expression of NotchICD. Importantly, derivation and evaluation of several independent populations of each NotchICD showed consistent CBF-1 reporter activation that was not significantly different between hNotch2ICD and mNotch4ICD. These data demonstrate that Notch signaling can be amplified in MDA-MB-231 cells, and that stable expression of either hNotch2ICD or mNotch4ICD lead to comparable levels of CBF-1 reporter transactivation.

Figure 1D:
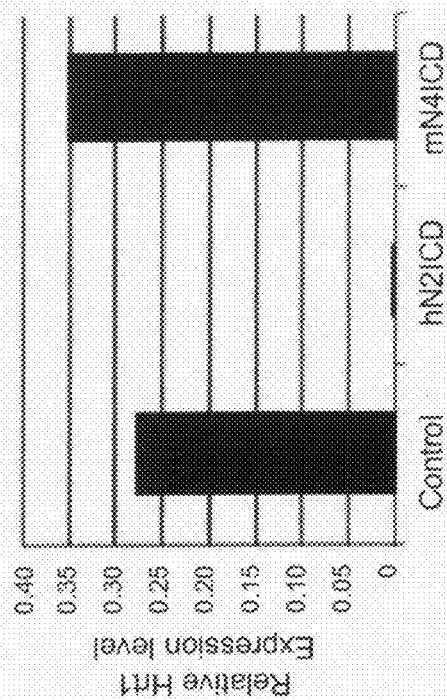
Figure 1A:
Figure 1C:
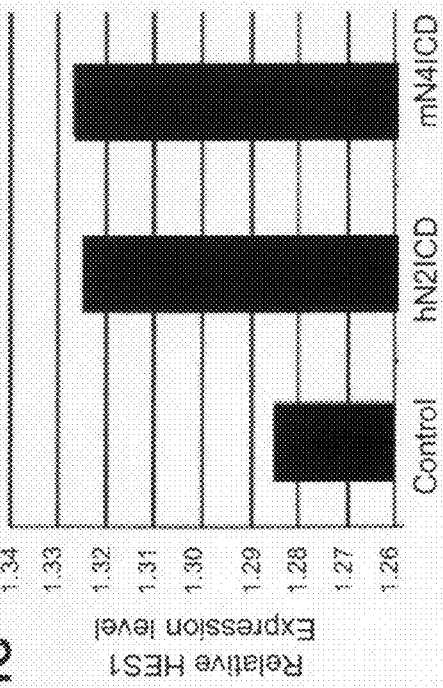

An analysis of the Notch transcriptional targets, HES1 and HRT1, was performed to detect possible variation in Notch effector target expression. Although no differences were observed in the cell populations by real time PCR for HES1 transcript (FIG. 1C), a HES1 promoter reporter showed decreased activation by hNotch2ICD in relation to mNotch4ICD (1.7 fold higher, p=0.05). A striking difference was the expression of Hrt1, which was high in all cell populations with the exception of hNotch2ICD (FIG. 1D). In comparison with the control, it appears that hNotch2ICD has a selective effect in suppressing Hrt1 expression, suggesting a possible mechanism of differential signaling via the Notch 2 pathway.

Experimental Example 3

Effect of Notch Pathways on Characteristics of Malignancy

A. Differential Effects of hNotch2ICD and mNotch4ICD on Cell Growth and Density

Figure 2B:
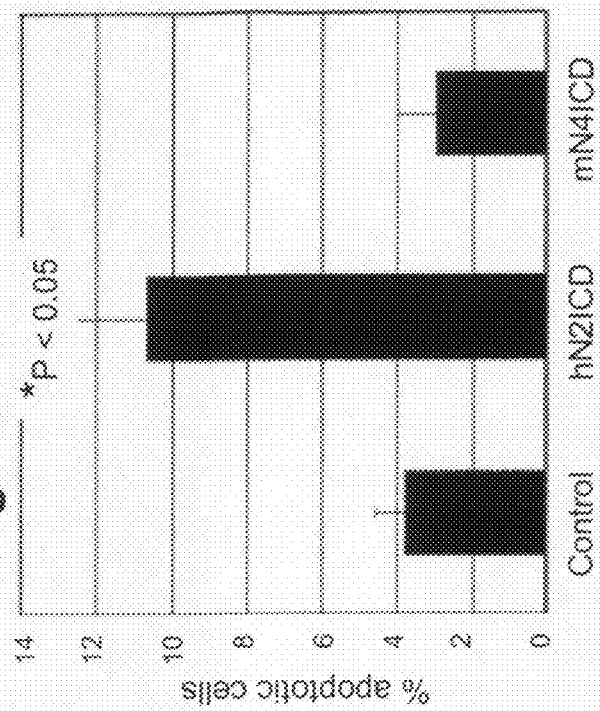
FIGS. 2A-2E, is a series of images illustrating how NotchICD affects cell proliferation and survival in MDA-MB-231 stable transfectants.
Figure 2A:
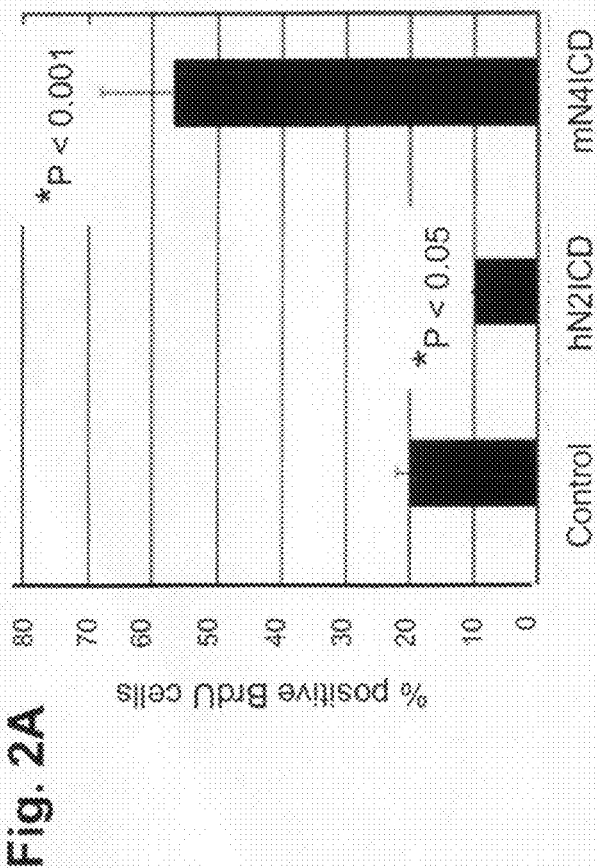

Studies were performed to assess the characteristics of malignancy following activation of the Notch 2 and Notch 4 pathways using growth curve analysis. Activation of the Notch 2 signaling led to decreased rates of growth whereas activation of Notch 4 signaling led to rapid cell growth and higher cell density. The hNotch2ICD cells had an approximate 3-fold reduction in cells number at peak density compared to mNotch4ICD signaling. To quantify rates of cell proliferation, BrdU incorporation was used to quantify cells in S-phase. The decrease in S-phase cells in the hNotch2ICD correlated with the growth curve, as mNotch4ICD had 1.5- fold as many S-phase cells compared to control (p<0.05, FIG. 2A), and 2-fold as many labeled cells compared to hNotch2ICD (p<0.05, FIG. 2A). Since different rates of apoptosis can also account for changes in cell number, TUNEL was used to quantify apoptosis rates. hNotch2ICD cells had a 2.5-fold increase in apoptotic cells (P<0.05, FIG. 2B) compared to control. There was no significant differences in apoptosis in mNotch4ICD and control cell populations (FIG. 2B).

B. Effect of Notch Signaling on Malignant Cell's Ability to Grow Independent of Extracellular Signals.

Figure 2C:
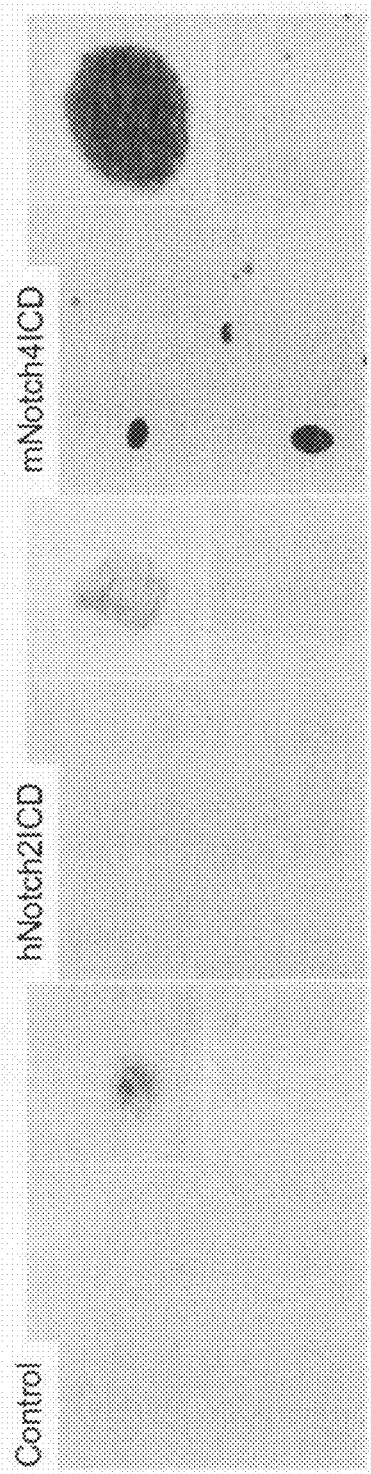
Figure 2E:
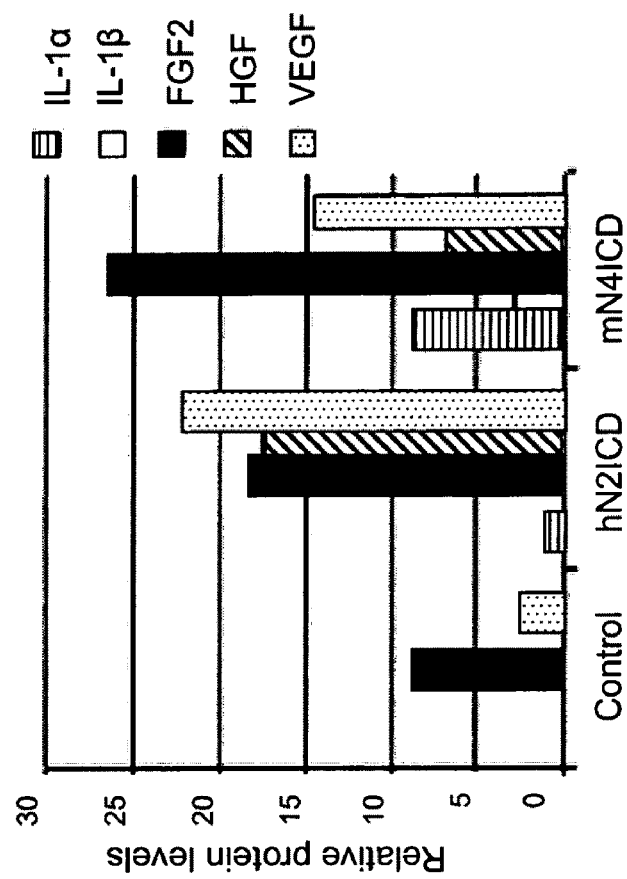
Figure 2D:
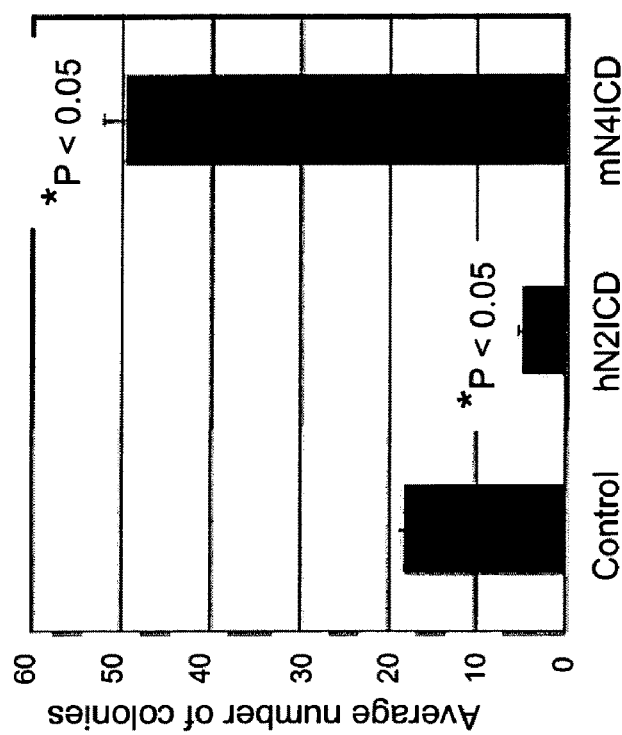

A characteristic of malignant cells is their ability to grow independently of extracellular signals and matrix interactions. Since activated Notch may differentially regulate adherent cell growth versus anchorage independent growth31, cell survival was tested at clonal plating density or in soft agar. The hNotch2ICD led to impaired adherent clonal growth, resulting in decreased colony number (2-fold, p<0.05) and decreased growth area (2-fold, p<0.05). Similarly, Notch 2 activation led to impaired growth in soft agar, with more than 3-fold decrease in colony number (p<0.05, FIGS. 2C, 2D). On the other hand, mNotch4ICD cells showed a growth and survival advantage in both assays, with increased adherent growth at clonal density (p<0.01), and increased soft agar colonies (FIGS. 2C, D). To determine if the MDA-MB-231 cells expressing hNotch21ICD had a growth/survival deficiency due to lack of survival factors (e.g. VEGF and FGF), levels of secreted cytokines were determined in the tumor cell conditioned medium (FIG. 2E). The cells expressing activated forms of Notch had higher levels of cytokines than control. Both Notch 2 and Notch4 activation increases VEGF, hepatocyte growth factor (HGF), interleukin-1a and FGF-1, all factors that may affect vascular recruitment.

Experimental Example 4 hNotch2ICD Suppresses the Malignant Phenotype of MDA-MB-231 Mammary Carcinoma Cells In order to determine if the decreased proliferation and survival of malignant breast tumor cells induced by hNotch2ICD would correlate to impaired growth in vivo, xenografts of tumor cells were implanted into immunocompromised mice which support tumor growth of MDA-MB-231 cells.

A subcutaneous injection of MDA-MB-231 cells was made into the right flank of immunocompromised mice. 100% of nude mice injected with control MDA-MD-231 cells developed tumors with a latency of ~1 week. The tumors continued to grow with a doubling volume in the fastest rate of growth of about 1 week. Activation of Notch 2 signaling significantly suppressed the malignant phenotype, since only 42% of the hNotch2ICD mice generated tumors. The tumor-free mice were maintained for four months and never exhibited any tumor growth. In the mice that did grow tumors from hNotch2ICD cells, the tumors were significantly smaller that control, with a longer latency to formation.

Figure 3A:
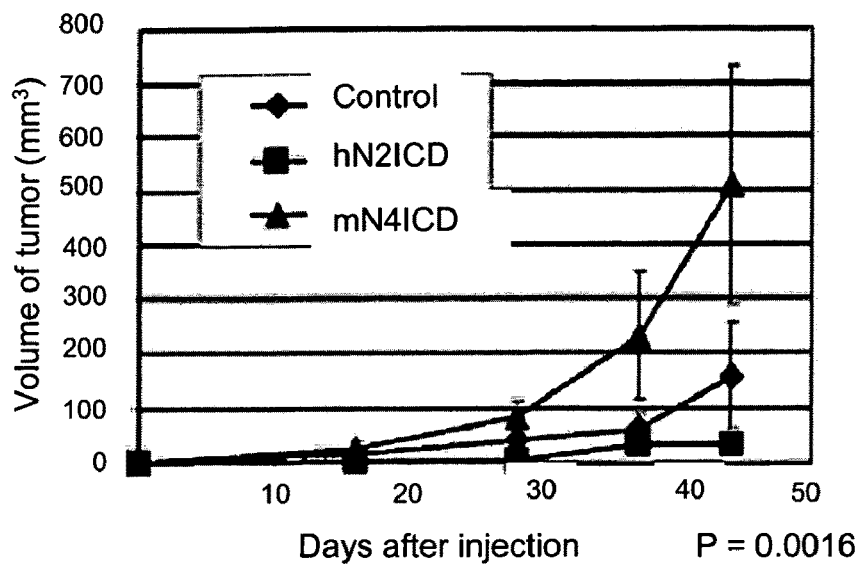
FIGS. 3A-3C, is a series of images depicting how Notch 2 signaling mediates a tumor suppressor xenograft phenotype.

This phenotype stands in stark contrast to mice injected with tumor cells with mNotch4ICD activation. 100% of this group exhibited tumors, but the tumors had a shorter latency period, increased growth rate and larger final size than the control tumors (FIG. 3A). The mNotch4ICD tumors had an increased peak doubling time compared to controls, doubling volume approximately every 5 days.

Figure 3B:
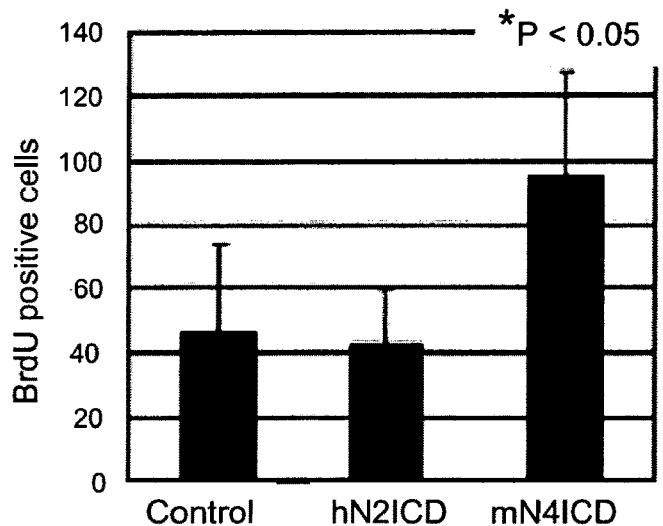
Figure 3C:
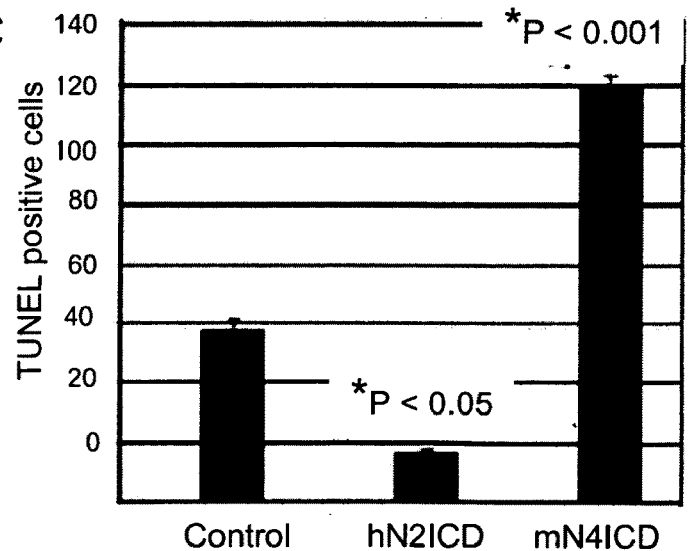

These phenotypes were further analyzed for proliferation at the end of the experiments (FIG. 3B), since tumors from mNotch4ICD had significantly increased proliferation. However, tumor apoptotic indices at the end of the experiment did not correspond with final size (FIG. 2C), since hNotch2ICD had low levels of apoptosis, and mNotch4ICD had elevated apoptosis, presumably due to the large size of the tumors limiting vascular perfusion.

Morphologically, all of the tumors demonstrated characteristics consistent with lobular adenocarcinoma (FIG. 4). These include the "signet ring" cell morphology, in which mucin accumulation has pushed the nucleus toward the cell's periphery and the high levels of vascularization, apparent by high capillary density. The control and hNotch2ICD tumors, which were the smallest tumors, displayed significant levels of necrosis within the tumor core, with inflammatory infiltrate and regions of hemorrhage. In some cases necrosis in these groups extended to the subdermal region. No evidence of invasive growth was observed in the control of hNotch2ICD tumors. In contrast, the mNotch4ICD tumors, while greater than 4-fold the size of the control/hNotch2ICD group, had low levels of necrosis and densely packed tumor cells in the tumor's core region. It was frequent to find that mNotch4ICD tumors has already invaded the peritoneum.

Experimental Example 5

Activation of Notch Signaling Leads to Increased Vascularization in Xenografts

In order to further investigate blood vessel recruitment in xenograft model, expression of blood endothelial (PECAM and MECA-32) and lymphatic endothelial (LYVE-1) cells in the tumor vasculature were quantified.

Figure 6A:
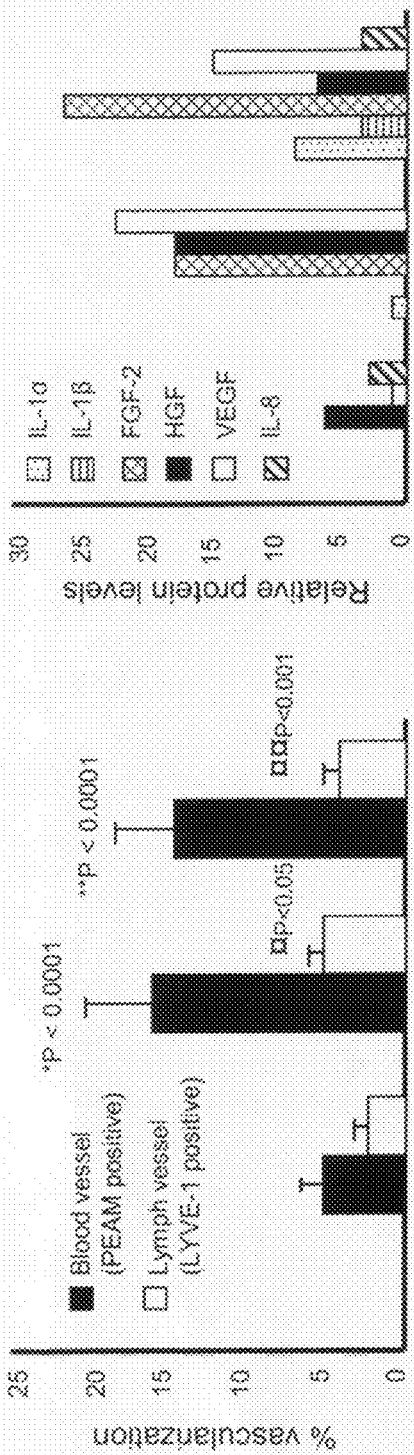
FIGS. 6A-6D, is a series of images demonstrating that NotchICD differentially regulates tumor vascularization and angiogenic cytokine production.

Activation of Notch signaling in vitro leads to increased secretion of survival/angiogenic cytokines. PECAM was used to quantify blood vessels (FIG. 5A). hNotch2ICD and mNotch4ICD had comparable areas of vascularization per tumor area with an approximately 2-fold increase in blood vessel density compared to control tumors ($p<0.0001$). The lymphendothelial cell marker LYVE-1 was used in conjunction with the blood endothelial cell marker MECA-32 to differentiate between lymphatic and blood vessels. Specific staining of blood vessels was observed in the MECA-32 stained sections, as adjoining tumor cell-filled lymphatic vessels showed staining distinct from adjacent blood vessels (FIG. 5B, white arrows). There was a marked increase in the area of both blood vessels and lymphatic vessels in the hNotch2ICD and mNotch4ICD tumors compared to control, despite their contrasting growth phenotypes. Blood vessels in the mNotch4ICD tumors were typically found clustered in hot spots along the perimeter of tumors, while blood vessels in the hNotch2ICD tumors were present throughout the tumor. Additionally, the lymphatic vessels of both hNotch2ICD and mNotch4ICD were large, with tumor cells completely filling some vessels, in comparison to blood vessels, which were smaller and contained only blood cells, inflammatory cells and a few tumore cells. Surprisingly, the overall extent of vascularization was comparable between hNotch2ICD and mNotch4ICD tumors (FIG. 6A).

Experimental Example 6

Distinct Angiogenic Cytokines are Produced by NotchICD Tumor Versus Host

In order to address the possibility that secretion of angiogenic cytokines by the tumor/host may provide a mechanistic basis for variation, plasma from tumor bearing mice was collected at several time points during the course of the xenograft experiment (before inoculation, days 14, 28 and 44 (FIG. 3A) and used to determine the release of human agiongenic cytokines from the tumor cells.

Figure 6B:
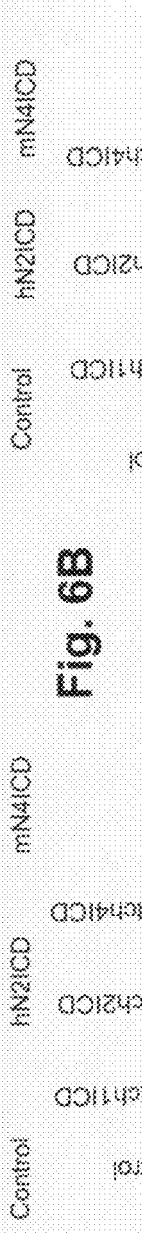

The highest levels of angiogenic factors over the course of the experiments was observed at day 28 after inoculation, and mice with hNotch2ICD and mNotch4ICD tumors expressed higher levels of cytokines compared to control tumors, in particular HGF and FGF-1. These data match the in vitro results (FIGS. 2E and 6B).

Experimental Example 7

RT-PCR

To further understand differences in factors regulating vessel recruitment, mouse of human specific primers were generated to identify cytokine transcripts from tumor cells versus mouse stroma.

Figure 6C:
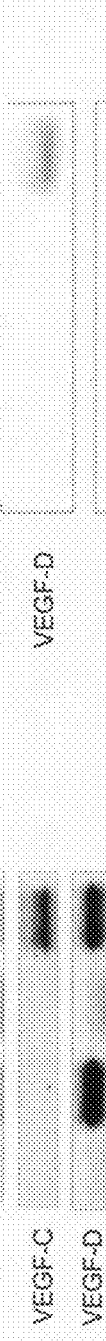

RNA was collected from tumors at the end of the experiments, 44 days after injection. mNotch4ICD selectively expressed VEGF-C, VEGF-D and placental growth factor (PIGF). Unlike the rest of the tumors, however it did not express detectable levels of FGF-1. Additionally, hNotch2ICD tumors had lower levels of transcripts for angiopoietin-1 (Ang-1), NRP-1 and NRP-2 compared to other tumor groups (FIG. 6C).

Figure 6D:
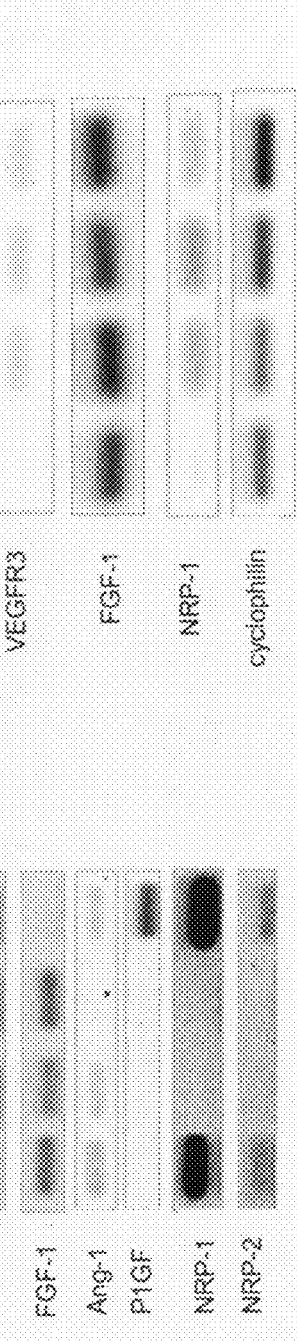

Analysis was also performed with mouse specific primers to detect host derived cytokines (FIG. 6D). No mouse VEGF-A, VEGF-B, or VEGF-c were detected in any tumors, however mNotch4ICD also contains mouse VEGF-D transcripts.

Experimental Example 8 hNotch1ICD Inhibits MDA-MB-231 Tumor Growth in the Mammary Fat Pad

It has been well documented that tumor site influences tumor growth. In order to assess the influence host microenvironmental factors might have upon tumor phenotype regulation, mammary xenografts were used to extend the xenograft model.

In a second xenograft model, tumor cells were inoculated into the mammary fat pad. As in the subcutaneous xenograft model, hNotch2ICD expression suppressed xenograft growth, while mNotch4ICD promoted tumor growth (FIG. 7A). The mice in all groups generated palpable tumors by two weeks after injection, however the tumors in the hNotch2ICD group regressed and surprisingly disappeared in 60% of the mice alive after 33 days after injection. The remaining hNotch2ICD tumors were extremely small. Histologically, the tumors demonstrated similar characteristics to the subcutaneous tumors as well as to the lobular adenocarcinoma.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inhibiting the growth of a breast cancer cell in a human having breast cancer, said method comprising administering to said human an isolated polypeptide consisting of the intracellular domain of human Notch 2 (hNotch2ICD) as set forth in SEQ ID NO: 3, wherein said polypeptide inhibits the growth of said breast cancer cell.

2. The method of claim 1, wherein said polypeptide further comprises a detectable label.

* * * * *

SEQUENCE LISTING

<160> NUMBER OF SEQ ID NOS: 5

<210> SEQ ID NO 1
<211> LENGTH: 11433
<212> TYPE: DNA
<213> ORGANISM: Homo sapiens

<400> SEQUENCE: 1

| | | | | | |
|---|---|---|---|---|---|
| aggctgcttc | gttgcacacc | cgagaaagtt | tcagccaaac | ttcgggcggc | ggctgaggcg | 60 |
| gcggccgagg | agcggcggac | tcggggcgcg | gggagtcgag | gcatttgcgc | ctgggcttcg | 120 |
| gagcgtagcg | ccagggcctg | agcctttgaa | gcaggaggag | gggaggagag | agtggggctc | 180 |
| ctctatcggg | acccccctccc | catgtggatc | tgcccaggcg | gcggcggcgg | cggcggagga | 240 |
| ggaggcgacc | gagaagatgc | ccgccctgcg | ccccgctctg | ctgtgggcgc | tgctggcgct | 300 |
| ctggctgtgc | tgcgcggccc | ccgcgcatgc | attgcagtgt | cgagatggct | atgaaccctg | 360 |
| tgtaaatgaa | ggaatgtgtg | ttacctacca | caatggcaca | ggatactgca | aatgtccaga | 420 |
| aggcttcttg | ggggaatatt | gtcaacatcg | agacccctgt | gagaagaacc | gctgccagaa | 480 |
| tggtgggact | tgtgtggccc | aggccatgct | ggggaaagcc | acgtgccgat | gtgcctcagg | 540 |
| gtttacagga | gaggactgcc | agtactcaac | atctcatcca | tgctttgtgt | ctcgaccctg | 600 |
| cctgaatggc | ggcacatgcc | atatgctcag | ccgggatacc | tatgagtgca | cctgtcaagt | 660 |
| cgggtttaca | ggtaaggagt | gccaatggac | ggatgcctgc | ctgtctcatc | cctgtgcaaa | 720 |
| tggaagtacc | tgtaccactg | tggccaacca | gttctcctgc | aaatgcctca | caggcttcac | 780 |
| agggcagaaa | tgtgagactg | atgtcaatga | gtgtgacatt | ccaggacact | gccagcatgg | 840 |
| tggcacctgc | ctcaacctgc | ctggttccta | ccagtgccag | tgccctcagg | gcttcacagg | 900 |
| ccagtactgt | gacagcctgt | atgtgccctg | tgcaccctca | ccttgtgtca | atggaggcac | 960 |
| ctgtcggcag | actggtgact | tcacttttga | gtgcaactgc | cttccaggtt | ttgaagggag | 1020 |
| cacctgtgag | aggaatattg | atgactgccc | taaccacagg | tgtcagaatg | gagggtttg | 1080 |
| tgtggatggg | gtcaacactt | acaactgccg | ctgtccccca | caatggacag | acagttctg | 1140 |
| cacagaggat | gtggatgaat | gcctgctgca | gcccaatgcc | tgtcaaaatg | ggggcacctg | 1200 |
| tgccaaccgc | aatggaggct | atggctgtgt | atgtgtcaac | ggctggagtg | gagatgactg | 1260 |
| cagtgagaac | attgatgatt | gtgccttcgc | ctcctgtact | ccaggctcca | cctgcatcga | 1320 |
| ccgtgtggcc | tccttctctt | gcatgtgccc | agagggggaag | gcaggtctcc | tgtgtcatct | 1380 |
| ggatgatgca | tgcatcagca | atccttgcca | caaggggggca | ctgtgtgaca | ccaacccccct | 1440 |
| aaatgggcaa | tatatttgca | cctgcccaca | aggctacaaa | ggggctgact | gcacagaaga | 1500 |
| tgtggatgaa | tgtgccatgg | ccaatagcaa | tccttgtgag | catgcaggaa | aatgtgtgaa | 1560 |
| cacgatggc | gccttccact | gtgagtgtct | gaagggttat | gcaggacctc | gttgagagat | 1620 |
| ggacatcaat | gagtgccatt | cagacccctg | ccagaatgat | gctacctgtc | tggataagat | 1680 |
| tggaggcttc | acatgtctgt | gcatgccagg | tttcaaaggt | gtgcattgtg | aattagaaat | 1740 |
| aaatgaatgt | cagagcaacc | cttgtgtgaa | caatgggcag | tgtgtggata | agtcaatcg | 1800 |
| tttccagtgc | ctgtgtcctc | ctggtttcac | tgggccagtt | tgccagattg | atattgatga | 1860 |
| ctgttccagt | actccgtgtc | tgaatgggc | aaagtgtatc | gatcacccga | atggctatga | 1920 |
| atgccagtgt | gccacaggtt | tcactggtgt | gttgtgtgag | gagaacattg | acaactgtga | 1980 |
| ccccgatcct | tgccaccatg | gtcagtgtca | ggatggtatt | gattcctaca | cctgcatctg | 2040 |

```
caatcccggg tacatgggcg ccatctgcag tgaccagatt gatgaatgtt acagcagccc    2100
ttgcctgaac gatggtcgct gcattgacct ggtcaatggc taccagtgca actgccagcc    2160
aggcacgtca ggggttaatt gtgaaattaa ttttgatgac tgtgcaagta acccttgtat    2220
ccatggaatc tgtatggatg cattaatcg ctacagttgt gtctgctcac caggattcac     2280
agggcagaga tgtaacattg acattgatga gtgtgcctcc aatccctgtc gcaagggtgc    2340
aacatgtatc aacggtgtga atggtttccg ctgtatatgc cccgagggac cccatcaccc    2400
cagctgctac tcacaggtga acgaatgcct gagcaatccc tgcatccatg gaaactgtac    2460
tggaggtctc agtggatata agtgtctctg tgatgcaggc tgggttggca tcaactgtga    2520
agtggacaaa aatgaatgcc tttcgaatcc atgccagaat ggaggaactt gtgacaatct    2580
ggtgaatgga tacaggtgta cttgcaagaa gggctttaaa ggctataact gccaggtgaa    2640
tattgatgaa tgtgcctcaa atccatgcct gaaccaagga acctgctttg atgacataag    2700
tggctacact tgccactgtg tgctgccata cacaggcaag aattgtcaga cagtattggc    2760
tccctgttcc ccaaacccctt gtgagaatgc tgctgtttgc aaagagtcac caaattttga    2820
gagttatact tgcttgtgtg ctcctggctg gcaaggtcag cggtgtacca ttgacattga    2880
cgagtgtatc tccaagccct gcatgaacca tggtctctgc cataacaccc agggcagcta    2940
catgtgtgaa tgtccaccag gcttcagtgg tatggactgt gaggaggaca ttgatgactg    3000
ccttgccaat ccttgccaga atggaggttc ctgtatggat ggagtgaata ctttctcctg    3060
cctctgcctt ccgggtttca ctggggataa gtgccagaca gacatgaatg agtgtctgag    3120
tgaaccctgt aagaatggag ggacctgctc tgactacgtc aacagttaca cttgcaagtg    3180
ccaggcagga tttgatggag tccattgtga gaacaacatc aatgagtgca ctgagagctc    3240
ctgtttcaat ggtggcacat gtgttgatgg gattaactcc ttctcttgct tgtgccctgt    3300
gggtttcact ggatccttct gcctccatga gatcaatgaa tgcagctctc atccatgcct    3360
gaatgaggga acgtgtgttg atggcctggg tacctaccgc tgcagctgcc ccctgggcta    3420
cactgggaaa aactgtcaga ccctggtgaa tctctgcagt cggtctccat gtaaaaacaa    3480
aggtacttgc gttcagaaaa aagcagagtc ccagtgccta tgtccatctg gatgggctgg    3540
tgcctattgt gacgtgccca atgtctcttg tgacatagca gcctccagga gaggtgtgct    3600
tgttgaacac ttgtgccagc actcaggtgt ctgcatcaat gctggcaaca cgcattactg    3660
tcagtgcccc ctgggctata ctgggagcta ctgtgaggag caactcgatg agtgtgcgtc    3720 caaccccctgc cagcacgggg caacatgcag tgacttcatt ggtggataca gatgcgagtg    3780
tgtcccaggc tatcagggtg tcaactgtga gtatgaagtg gatgagtgcc agaatcagcc    3840
ctgccagaat ggaggcacct gtattgacct tgtgaaccat ttcaagtgct cttgcccacc    3900
aggcactcgg ggcctactct gtgaagagaa cattgatgac tgtgcccggg tccccattg     3960 ccttaatggt ggtcagtgca tggataggat tggaggctac agttgtcgct gcttgcctgg    4020
ctttgctggg gagcgttgtg agggagacat caacgagtgc ctctccaacc cctgcagctc    4080
tgagggcagc ctggactgta tacagctcac caatgactac ctgtgtgttt gccgtagtgc    4140
ctttactggc cggcactgtg aaaccttcgt cgatgtgtgt ccccagatgc cctgcctgaa    4200
tggagggact tgtgctgtgg ccagtaacat gcctgatggt ttcatttgcc gttgtccccc    4260
gggattttcc ggggcaaggt gccagagcag ctgtggacaa gtgaaatgta ggaagggga    4320 gcagtgtgtg cacaccgcct ctggaccccg ctgcttctgc cccagtcccc gggactgcga    4380
```

```
gtcaggctgt gccagtagcc cctgccagca cggggggcagc tgccaccctc agcgccagcc    4440
tccttattac tcctgccagt gtgccccacc attctcgggt agccgctgtg aactctacac    4500
ggcacccccc agcacccctc ctgccacctg tctgagccag tattgtgccg acaaagctcg    4560
ggatggcgtc tgtgatgagg cctgcaacag ccatgcctgc cagtgggatg ggggtgactg    4620
ttctctcacc atggagaacc cctgggccaa ctgctcctcc ccacttccct gctgggatta    4680
tatcaacaac cagtgtgatg agctgtgcaa cacggtcgag tgcctgtttg acaactttga    4740
atgccagggg aacagcaaga catgcaagta tgacaaatac tgtgcagacc acttcaaaga    4800
caaccactgt gaccagggt gcaacagtga ggagtgtggt tgggatgggc tggactgtgc    4860
tgctgaccaa cctgagaacc tggcagaagg taccctggtt attgtggtat tgatgccacc    4920
tgaacaactg ctccaggatg ctcgcagctt cttgcgggca ctgggtaccc tgctccacac    4980
caacctgcgc attaagcggg actcccaggg ggaactcatg gtgtacccct attatggtga    5040
gaagtcagct gctatgaaga acagaggat gacacgcaga tcccttcctg gtgaacaaga    5100
acaggaggtg gctggctcta aagtctttct ggaaattgac aaccgccagt gtgttcaaga    5160
ctcagaccac tgcttcaaga acacggatgc agcagcagct ctcctggcct ctcacgccat    5220
acaggggacc ctgtcatacc ctcttgtgtc tgtcgtcagt gaatccctga ctccagaacg    5280
cactcagctc ctctatctcc ttgctgttgc tgttgtcatc attctgttta ttattctgct    5340
gggggtaatc atggcaaaac gaaagcgtaa gcatggctct ctctggctgc ctgaaggttt    5400
cactcttcgc cgagatgcaa gcaatcacaa gcgtcgtgag ccagtgggac aggatgctgt    5460
ggggctgaaa aatctctcag tgcaagtctc agaagctaac ctaattggta ctggaacaag    5520
tgaacactgg gtcgatgatg aagggcccca gccaaagaaa gtaaaggctg aagatgaggc    5580
cttactctca gaagaagatg accccattga tcgacggcca tggacacagc agcaccttga    5640
agctgcagac atccgtagga caccatcgct ggctctcacc cctcctcagg cagagcagga    5700
ggtggatgtg ttagatgtga atgtccgtgg cccagatggc tgcaccccat tgatgttggc    5760
ttctctccga ggaggcagct cagatttgag tgatgaagat gaagatgcag aggactcttc    5820
tgctaacatc atcacagact tggtctacca gggtgccagc ctccaggccc agacagaccg    5880
gactggtgag atggccctgc accttgcagc ccgctactca cgggctgatg ctgccaagcg    5940
tctcctggat gcaggtgcag atgccaatgc ccaggacaac atgggccgct gtccactcca    6000
tgctgcagtg gcagctgatg cccaaggtgt cttccagatt ctgattcgca accgagtaac    6060
tgatctagat gccaggatga atgatggtac tacacccctg atcctggctg cccgcctggc    6120
tgtggaggga atggtggcag aactgatcaa ctgccaagcg gatgtgaatg cagtggatga    6180
ccatggaaaa tctgctcttc actgggcagc tgctgtcaat aatgtggagg caactctttt    6240
gttgttgaaa aatggggcca accgagacat gcaggacaac aaggaagaga cacctctgtt    6300
tcttgctgcc cggagggga gctatgaagc agccaagatc tgttagacc attttgccaa    6360 tcgagacatc acagaccata tggatcgtct tccccgggat gtggctcggg atcgcatgca    6420
ccatgacatt gtgcgccttc tggatgaata caatgtgacc ccaagccctc aggcaccgt    6480 gttgacttct gctctctcac ctgtcatctg tgggcccaac agatcttcc tcagcctgaa    6540 gcacacccca atgggcaaga gtctagacg gcccagtgcc aagagtacca tgcctactag    6600
cctccctaac cttgccaagg aggcaaagga tgccaagggt agtaggagga agaagtctct    6660
gagtgagaag gtccaactgt ctgagagttc agtaacttta tccctgttg attccctaga    6720 atctcctcac acgtatgttt ccgacaccac atccctccca atgattacat ccctgggat    6780
```

```
cttacaggcc tcacccaacc ctatgttggc cactgccgcc cctcctgccc cagtccatgc   6840
ccagcatgca ctatcttttt ctaaccttca tgaaatgcag cctttggcac atggggccag   6900
cactgtgctt ccctcagtga gccagttgct atcccaccac cacattgtgt ctccaggcag   6960
tggcagtgct ggaagcttga gtaggctcca tccagtccca gtcccagcag attggatgaa   7020
ccgcatggag gtgaatgaga cccagtacaa tgagatgttt ggtatggtcc tggctccagc   7080
tgagggcacc catcctggca tagctcccca gagcaggcca cctgaaggga agcacataac   7140
cacccctcgg gagcccttgc ccccattgt gactttccag ctcatcccta aaggcagtat   7200
tgcccaacca gcgggggctc cccagcctca gtccacctgc cctccagctg ttgcgggccc   7260
cctgcccacc atgtaccaga ttccagaaat ggcccgtttg cccagtgtgg ctttccccac   7320
tgccatgatg ccccagcagg acgggcaggt agctcagacc attctcccag cctatcatcc   7380
tttcccagcc tctgtgggca agtacccac acccccttca cagcacagtt atgcttcctc   7440
aaatgctgct gagcgaacac ccagtcacag tggtcacctc cagggtgagc atccctacct   7500
gacaccatcc ccagagtctc ctgaccagtg gtcaagttca tcaccccact ctgcttctga   7560
ctggtcagat gtgaccacca gccctacccc tgggggtgct ggaggaggtc agcggggacc   7620
tgggacacac atgtctgagc caccacacaa caacatgcag gtttatgcgt gagagagtcc   7680
acctccagtg tagagacata actgactttt gtaaatgctg ctgaggaaca aatgaaggtc   7740
atccgggaga gaaatgaaga aatctctgga gccagcttct agaggtagga aagagaagat   7800
gttcttattc agataatgca agagaagcaa ttcgtcagtt tcactgggta tctgcaaggc   7860
ttattgatta ttctaatcta ataagacaag tttgtggaaa tgcaagatga atacaagcct   7920
tgggtccatg tttactctct tctatttgga gaataagatg gatgcttatt gaagcccaga   7980
cattcttgca gcttggactg cattttaagc cctgcaggct tctgccatat ccatgagaag   8040
attctacact agcgtcctgt tgggaattat gccctggaat tctgcctgaa ttgacctacg   8100
catctcctcc tccttggaca ttcttttgtc ttcatttggt gcttttggtt ttgcacctct   8160
ccgtgattgt agcccctacca gcatgttata gggcaagacc tttgtgcttt tgatcattct   8220
ggcccatgaa agcaactttg gtctccttc ccctcctgtc ttcccggtat cccttggagt   8280
ctcacaaggt ttactttggt atggttctca gcacaaacct ttcaagtatg ttgtttcttt   8340
ggaaaatgga catactgtat tgtgttctcc tgcatatatc attcctggag agagaagggg   8400
agaagaatac ttttcttcaa caaattttgg gggcaggaga tcccttcaag aggctgcacc   8460 ttaattttc ttgtctgtgt gcaggtcttc atataaactt taccaggaag aagggtgtga   8520
gtttgttgtt tttctgtgta tgggcctggt cagtgtaaag ttttatcctt gatagtctag   8580
ttactatgac cctccccact tttttaaaac cagaaaaagg tttggaatgt tggaatgacc   8640
aagagacaag ttaactcgtg caagagccag ttacccaccc acaggtcccc ctacttcctg   8700
ccaagcattc cattgactgc ctgtatggaa cacatttgtc ccagatctga gcattctagg   8760 cctgttcac tcactcaccc agcatatgaa actagtctta actgttgagc ctttcctttc   8820
atatccacag aagacactgt ctcaaatgtt gtaccctgc catttaggac tgaactttcc   8880
ttagcccaag ggacccagtg acagttgtct tccgtttgtc agatgatcag tctctactga   8940
ttatcttgct gcttaaaggc ctgctcacca atctttcttt cacaccgtgt ggtccgtgtt   9000
actggtatac ccagtatgtt ctcactgaag acatggactt tatatgttca agtgcaggaa   9060
ttggaaagtt ggacttgttt tctatgatcc aaaacagccc tataagaagg ttggaaaagg   9120
```

```
aggaactata tagcagcctt tgctattttc tgctaccatt tcttttcctc tgaagcggcc   9180
atgacattcc ctttggcaac taacgtagaa actcaacaga acattttcct ttcctagagt   9240 cacctttag atgataatgg acaactatag acttgctcat tgttcagact gattgcccct    9300
cacctgaatc cactctctgt attcatgctc ttggcaattt ctttgacttt cttttaaggg   9360
cagaagcatt ttagttaatt gtagataaag aatagttttc ttcctcttct ccttgggcca   9420
gttaataatt ggtccatggc tacactgcaa cttccgtcca gtgctgtgat gcccatgaca   9480
cctgcaaaat aagttctgcc tgggcatttt gtagatatta acaggtgaat tcccgactct   9540
tttggtttga atgacagttc tcattccttc tatggctgca agtatgcatc agtgcttccc   9600
acttacctga tttgtctgtc ggtggcccca tatggaaacc ctgcgtgtct gttggcataa   9660
tagtttacaa atggtttttt cagtcctatc caaatttatt gaaccaacaa aaataattac   9720
ttctgccctg agataagcag attaagtttg ttcattctct gctttattct ctccatgtgg   9780
caacattctg tcagcctctt tcatagtgtg caaacatttt atcattctaa atggtgactc   9840
tctgcccttg gacccattta ttattcacag atggggagaa cctatctgca tggacctctg   9900
tggaccacag cgtacctgcc cctttctgcc ctcctgctcc agccccactt ctgaaagtat   9960
cagctactga tccagccact ggatatttta tatcctccct tttccttaag cacaatgtca  10020
gaccaaattg cttgtttctt tttcttggac tactttaatt tggatccttt gggtttggag  10080
aaagggaatg tgaaagctgt cattacagac aacaggtttc agtgatgagg aggacaacac  10140
tgcctttcaa acttttact gatctcttag atttttaagaa ctcttgaatt gtgtggtatc   10200
taataaaagg gaaggtaaga tggataatca ctttctcatt tgggttctga attggagact  10260 cagttttat gagacacatc ttttatgcca tgtatagatc ctcccctgct attttggtt    10320 tattttatt gttataaatg ctttctttct ttgactcctc ttctgcctgc ctttggggat   10380
aggttttttt gtttgtttat ttgcttcctc tgttttgttt taagcatcat tttcttatgt  10440
gaggtgggga agggaaaggt atgagggaaa gagagtctga gaattaaaat attttagtat  10500
aagcaattgg ctgtgatgct caaatccatt gcatcctctt attgaatttg ccaatttgta  10560 attttgcat aataaagaac caaaggtgta atgttttgtt gagaggtggt ttagggattt   10620
tggccctaac caatacattg aatgtatgat gactatttgg gaggacacat ttatgtaccc  10680
agaggccccc actaataagt ggtactatgg ttacttcctt gtgtacattt ctcttaaaag  10740
tgatattata tctgtttgta tgagaaaccc agtaaccaat aaaatgaccg catattcctg  10800
actaaacgta gtaaggaaaa tgcacacttt gttttactt ttccgtttca ttctaaaggt   10860
agttaagatg aaatttatat gaaagcattt ttatcacaaa ataaaaaagg tttgccaagc  10920
tcagtggtgt tgtattttt attttccaat actgcatcca tggcctggca gtgttacctc   10980
atgatgtcat aatttgctga gagagcaaat tttctttct ttctgaatcc cacaaagcct   11040
agcaccaaac ttcttttttt cttcctttaa ttagatcata aataaatgat cctgggaaa   11100 aagcatctgt caaataggaa acatcacaaa actgagcact cttctgtgca ctagccatag  11160
ctggtgacaa acagatggtt gctcaggac aaggtgcctt ccaatggaaa tgcgaagtag   11220
ttgctatagc aagaattggg aactgggata taagtcataa tattaattat gctgttatgt  11280
aaatgattgg tttgtaacat tccttaagtg aaatttgtgt agaacttaat atacaggatt  11340
ataaaataat attttgtgta taaatttgtt ataagttcac attcatacat ttatttataa  11400
agtcagtgag atatttgaac atgaaaaaaa aaa                               11433
```

```
<210> SEQ ID NO 2
<211> LENGTH: 2471
<212> TYPE: PRT
<213> ORGANISM: Homo sapiens

<400> SEQUENCE: 2

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
            20                  25                  30

Glu Pro Cys Val Asn Glu Gly Met Cys Val Thr Tyr His Asn Gly Thr
        35                  40                  45

Gly Tyr Cys Lys Cys Pro Glu Gly Phe Leu Gly Glu Tyr Cys Gln His
    50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
    290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
        355                 360                 365

Ala Gly Leu Leu Cys His Leu Asp Asp Ala Cys Ile Ser Asn Pro Cys
    370                 375                 380
```

-continued

```
His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
    450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
        515                 520                 525

Cys Gln Ile Asp Ile Asp Asp Cys Ser Ser Thr Pro Cys Leu Asn Gly
    530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
        595                 600                 605

Asp Glu Cys Tyr Ser Ser Pro Cys Leu Asn Asp Gly Arg Cys Ile Asp
    610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
                645                 650                 655

Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
        675                 680                 685

Asn Pro Cys Arg Lys Gly Ala Thr Cys Ile Asn Gly Val Asn Gly Phe
    690                 695                 700

Arg Cys Ile Cys Pro Glu Gly His His Pro Ser Cys Tyr Ser Gln
705                 710                 715                 720

Val Asn Glu Cys Leu Ser Asn Pro Cys Ile His Gly Asn Cys Thr Gly
                725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
        755                 760                 765

Gly Gly Thr Cys Asp Asn Leu Val Asn Gly Tyr Arg Cys Thr Cys Lys
    770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
```

-continued

```
                805                 810                 815
Tyr Thr Cys His Cys Val Leu Pro Tyr Thr Gly Lys Asn Cys Gln Thr
                820                 825                 830
Val Leu Ala Pro Cys Ser Pro Asn Pro Cys Glu Asn Ala Ala Val Cys
                835                 840                 845
Lys Glu Ser Pro Asn Phe Glu Ser Tyr Thr Cys Leu Cys Ala Pro Gly
                850                 855                 860
Trp Gln Gly Gln Arg Cys Thr Ile Asp Ile Asp Glu Cys Ile Ser Lys
865                 870                 875                 880
Pro Cys Met Asn His Gly Leu Cys His Asn Thr Gln Gly Ser Tyr Met
                885                 890                 895
Cys Glu Cys Pro Pro Gly Phe Ser Gly Met Asp Cys Glu Glu Asp Ile
                900                 905                 910
Asp Asp Cys Leu Ala Asn Pro Cys Gln Asn Gly Gly Ser Cys Met Asp
                915                 920                 925
Gly Val Asn Thr Phe Ser Cys Leu Cys Leu Pro Gly Phe Thr Gly Asp
                930                 935                 940
Lys Cys Gln Thr Asp Met Asn Glu Cys Leu Ser Glu Pro Cys Lys Asn
945                 950                 955                 960
Gly Gly Thr Cys Ser Asp Tyr Val Asn Ser Tyr Thr Cys Lys Cys Gln
                965                 970                 975
Ala Gly Phe Asp Gly Val His Cys Glu Asn Asn Ile Asn Glu Cys Thr
                980                 985                 990
Glu Ser Ser Cys Phe Asn Gly Gly Thr Cys Val Asp Gly Ile Asn Ser
                995                1000                1005
Phe Ser Cys Leu Cys Pro Val Gly Phe Thr Gly Ser Phe Cys Leu
                1010                1015                1020
His Glu Ile Asn Glu Cys Ser Ser His Pro Cys Leu Asn Glu Gly
                1025                1030                1035
Thr Cys Val Asp Gly Leu Gly Thr Tyr Arg Cys Ser Cys Pro Leu
                1040                1045                1050
Gly Tyr Thr Gly Lys Asn Cys Gln Thr Leu Val Asn Leu Cys Ser
                1055                1060                1065
Arg Ser Pro Cys Lys Asn Lys Gly Thr Cys Val Gln Lys Lys Ala
                1070                1075                1080
Glu Ser Gln Cys Leu Cys Pro Ser Gly Trp Ala Gly Ala Tyr Cys
                1085                1090                1095
Asp Val Pro Asn Val Ser Cys Asp Ile Ala Ala Ser Arg Arg Gly
                1100                1105                1110
Val Leu Val Glu His Leu Cys Gln His Ser Gly Val Cys Ile Asn
                1115                1120                1125
Ala Gly Asn Thr His Tyr Cys Gln Cys Pro Leu Gly Tyr Thr Gly
                1130                1135                1140
Ser Tyr Cys Glu Glu Gln Leu Asp Glu Cys Ala Ser Asn Pro Cys
                1145                1150                1155
Gln His Gly Ala Thr Cys Ser Asp Phe Ile Gly Gly Tyr Arg Cys
                1160                1165                1170
Glu Cys Val Pro Gly Tyr Gln Gly Val Asn Cys Glu Tyr Glu Val
                1175                1180                1185
Asp Glu Cys Gln Asn Gln Pro Cys Gln Asn Gly Gly Thr Cys Ile
                1190                1195                1200
Asp Leu Val Asn His Phe Lys Cys Ser Cys Pro Pro Gly Thr Arg
                1205                1210                1215
```

-continued

Gly Leu Leu Cys Glu Glu Asn Ile Asp Asp Cys Ala Arg Gly Pro
    1220                1225                1230

His Cys Leu Asn Gly Gly Gln Cys Met Asp Arg Ile Gly Gly Tyr
    1235                1240                1245

Ser Cys Arg Cys Leu Pro Gly Phe Ala Gly Glu Arg Cys Glu Gly
    1250                1255                1260

Asp Ile Asn Glu Cys Leu Ser Asn Pro Cys Ser Ser Glu Gly Ser
    1265                1270                1275

Leu Asp Cys Ile Gln Leu Thr Asn Asp Tyr Leu Cys Val Cys Arg
    1280                1285                1290

Ser Ala Phe Thr Gly Arg His Cys Glu Thr Phe Val Asp Val Cys
    1295                1300                1305

Pro Gln Met Pro Cys Leu Asn Gly Gly Thr Cys Ala Val Ala Ser
    1310                1315                1320

Asn Met Pro Asp Gly Phe Ile Cys Arg Cys Pro Pro Gly Phe Ser
    1325                1330                1335

Gly Ala Arg Cys Gln Ser Ser Cys Gly Gln Val Lys Cys Arg Lys
    1340                1345                1350

Gly Glu Gln Cys Val His Thr Ala Ser Gly Pro Arg Cys Phe Cys
    1355                1360                1365

Pro Ser Pro Arg Asp Cys Glu Ser Gly Cys Ala Ser Ser Pro Cys
    1370                1375                1380

Gln His Gly Gly Ser Cys His Pro Gln Arg Gln Pro Pro Tyr Tyr
    1385                1390                1395

Ser Cys Gln Cys Ala Pro Pro Phe Ser Gly Ser Arg Cys Glu Leu
    1400                1405                1410

Tyr Thr Ala Pro Pro Ser Thr Pro Pro Ala Thr Cys Leu Ser Gln
    1415                1420                1425

Tyr Cys Ala Asp Lys Ala Arg Asp Gly Val Cys Asp Glu Ala Cys
    1430                1435                1440

Asn Ser His Ala Cys Gln Trp Asp Gly Gly Asp Cys Ser Leu Thr
    1445                1450                1455

Met Glu Asn Pro Trp Ala Asn Cys Ser Ser Pro Leu Pro Cys Trp
    1460                1465                1470

Asp Tyr Ile Asn Asn Gln Cys Asp Glu Leu Cys Asn Thr Val Glu
    1475                1480                1485

Cys Leu Phe Asp Asn Phe Glu Cys Gln Gly Asn Ser Lys Thr Cys
    1490                1495                1500

Lys Tyr Asp Lys Tyr Cys Ala Asp His Phe Lys Asp Asn His Cys
    1505                1510                1515

Asp Gln Gly Cys Asn Ser Glu Glu Cys Gly Trp Asp Gly Leu Asp
    1520                1525                1530

Cys Ala Ala Asp Gln Pro Glu Asn Leu Ala Glu Gly Thr Leu Val
    1535                1540                1545

Ile Val Val Leu Met Pro Pro Glu Gln Leu Leu Gln Asp Ala Arg
    1550                1555                1560

Ser Phe Leu Arg Ala Leu Gly Thr Leu Leu His Thr Asn Leu Arg
    1565                1570                1575

Ile Lys Arg Asp Ser Gln Gly Glu Leu Met Val Tyr Pro Tyr Tyr
    1580                1585                1590

Gly Glu Lys Ser Ala Ala Met Lys Lys Gln Arg Met Thr Arg Arg
    1595                1600                1605

-continued

```
Ser Leu Pro Gly Glu Gln Glu Gln Val Ala Gly Ser Lys Val
    1610            1615            1620

Phe Leu Glu Ile Asp Asn Arg Gln Cys Val Gln Asp Ser Asp His
    1625            1630            1635

Cys Phe Lys Asn Thr Asp Ala Ala Ala Leu Leu Ala Ser His
    1640            1645            1650

Ala Ile Gln Gly Thr Leu Ser Tyr Pro Leu Val Ser Val Val Ser
    1655            1660            1665

Glu Ser Leu Thr Pro Glu Arg Thr Gln Leu Leu Tyr Leu Leu Ala
    1670            1675            1680

Val Ala Val Val Ile Ile Leu Phe Ile Ile Leu Leu Gly Val Ile
    1685            1690            1695

Met Ala Lys Arg Lys Arg Lys His Gly Ser Leu Trp Leu Pro Glu
    1700            1705            1710

Gly Phe Thr Leu Arg Arg Asp Ala Ser Asn His Lys Arg Arg Glu
    1715            1720            1725

Pro Val Gly Gln Asp Ala Val Gly Leu Lys Asn Leu Ser Val Gln
    1730            1735            1740

Val Ser Glu Ala Asn Leu Ile Gly Thr Gly Thr Ser Glu His Trp
    1745            1750            1755

Val Asp Asp Glu Gly Pro Gln Pro Lys Lys Val Lys Ala Glu Asp
    1760            1765            1770

Glu Ala Leu Leu Ser Glu Glu Asp Asp Pro Ile Asp Arg Arg Pro
    1775            1780            1785

Trp Thr Gln Gln His Leu Glu Ala Ala Asp Ile Arg Arg Thr Pro
    1790            1795            1800

Ser Leu Ala Leu Thr Pro Pro Gln Ala Glu Gln Glu Val Asp Val
    1805            1810            1815

Leu Asp Val Asn Val Arg Gly Pro Asp Gly Cys Thr Pro Leu Met
    1820            1825            1830

Leu Ala Ser Leu Arg Gly Gly Ser Ser Asp Leu Ser Asp Glu Asp
    1835            1840            1845

Glu Asp Ala Glu Asp Ser Ser Ala Asn Ile Ile Thr Asp Leu Val
    1850            1855            1860

Tyr Gln Gly Ala Ser Leu Gln Ala Gln Thr Asp Arg Thr Gly Glu
    1865            1870            1875

Met Ala Leu His Leu Ala Ala Arg Tyr Ser Arg Ala Asp Ala Ala
    1880            1885            1890

Lys Arg Leu Leu Asp Ala Gly Ala Asp Ala Asn Ala Gln Asp Asn
    1895            1900            1905

Met Gly Arg Cys Pro Leu His Ala Ala Val Ala Ala Asp Ala Gln
    1910            1915            1920

Gly Val Phe Gln Ile Leu Ile Arg Asn Arg Val Thr Asp Leu Asp
    1925            1930            1935

Ala Arg Met Asn Asp Gly Thr Thr Pro Leu Ile Leu Ala Ala Arg
    1940            1945            1950

Leu Ala Val Glu Gly Met Val Ala Glu Leu Ile Asn Cys Gln Ala
    1955            1960            1965

Asp Val Asn Ala Val Asp Asp His Gly Lys Ser Ala Leu His Trp
    1970            1975            1980

Ala Ala Ala Val Asn Asn Val Glu Ala Thr Leu Leu Leu Leu Lys
    1985            1990            1995

Asn Gly Ala Asn Arg Asp Met Gln Asp Asn Lys Glu Glu Thr Pro
```

-continued

```
                2000                2005                2010
Leu Phe Leu Ala Ala Arg Glu Gly Ser Tyr Glu Ala Ala Lys Ile
            2015                2020                2025
Leu Leu Asp His Phe Ala Asn Arg Asp Ile Thr Asp His Met Asp
            2030                2035                2040
Arg Leu Pro Arg Asp Val Ala Arg Asp Arg Met His His Asp Ile
            2045                2050                2055
Val Arg Leu Leu Asp Glu Tyr Asn Val Thr Pro Ser Pro Pro Gly
            2060                2065                2070
Thr Val Leu Thr Ser Ala Leu Ser Pro Val Ile Cys Gly Pro Asn
            2075                2080                2085
Arg Ser Phe Leu Ser Leu Lys His Thr Pro Met Gly Lys Lys Ser
            2090                2095                2100
Arg Arg Pro Ser Ala Lys Ser Thr Met Pro Thr Ser Leu Pro Asn
            2105                2110                2115
Leu Ala Lys Glu Ala Lys Asp Ala Lys Gly Ser Arg Arg Lys Lys
            2120                2125                2130
Ser Leu Ser Glu Lys Val Gln Leu Ser Glu Ser Ser Val Thr Leu
            2135                2140                2145
Ser Pro Val Asp Ser Leu Glu Ser Pro His Thr Tyr Val Ser Asp
            2150                2155                2160
Thr Thr Ser Ser Pro Met Ile Thr Ser Pro Gly Ile Leu Gln Ala
            2165                2170                2175
Ser Pro Asn Pro Met Leu Ala Thr Ala Pro Pro Ala Pro Val
            2180                2185                2190
His Ala Gln His Ala Leu Ser Phe Ser Asn Leu His Glu Met Gln
            2195                2200                2205
Pro Leu Ala His Gly Ala Ser Thr Val Leu Pro Ser Val Ser Gln
            2210                2215                2220
Leu Leu Ser His His His Ile Val Ser Pro Gly Ser Gly Ser Ala
            2225                2230                2235
Gly Ser Leu Ser Arg Leu His Pro Val Pro Val Pro Ala Asp Trp
            2240                2245                2250
Met Asn Arg Met Glu Val Asn Glu Thr Gln Tyr Asn Glu Met Phe
            2255                2260                2265
Gly Met Val Leu Ala Pro Ala Glu Gly Thr His Pro Gly Ile Ala
            2270                2275                2280
Pro Gln Ser Arg Pro Pro Glu Gly Lys His Ile Thr Thr Pro Arg
            2285                2290                2295
Glu Pro Leu Pro Pro Ile Val Thr Phe Gln Leu Ile Pro Lys Gly
            2300                2305                2310
Ser Ile Ala Gln Pro Ala Gly Ala Pro Gln Pro Gln Ser Thr Cys
            2315                2320                2325
Pro Pro Ala Val Ala Gly Pro Leu Pro Thr Met Tyr Gln Ile Pro
            2330                2335                2340
Glu Met Ala Arg Leu Pro Ser Val Ala Phe Pro Thr Ala Met Met
            2345                2350                2355
Pro Gln Gln Asp Gly Gln Val Ala Gln Thr Ile Leu Pro Ala Tyr
            2360                2365                2370
His Pro Phe Pro Ala Ser Val Gly Lys Tyr Pro Thr Pro Pro Ser
            2375                2380                2385
Gln His Ser Tyr Ala Ser Ser Asn Ala Ala Glu Arg Thr Pro Ser
            2390                2395                2400
```

His Ser Gly His Leu Gln Gly Glu His Pro Tyr Leu Thr Pro Ser
    2405                2410                2415

Pro Glu Ser Pro Asp Gln Trp Ser Ser Ser Pro His Ser Ala
    2420                2425                2430

Ser Asp Trp Ser Asp Val Thr Thr Ser Pro Thr Pro Gly Gly Ala
    2435                2440                2445

Gly Gly Gly Gln Arg Gly Pro Gly Thr His Met Ser Glu Pro Pro
    2450                2455                2460

His Asn Asn Met Gln Val Tyr Ala
    2465                2470

<210> SEQ ID NO 3
<211> LENGTH: 769
<212> TYPE: PRT
<213> ORGANISM: Homo sapiens

<400> SEQUENCE: 3

Lys Arg Lys His Gly Ser Leu Trp Leu Pro Glu Gly Phe Thr Leu Arg
1               5                   10                  15

Arg Asp Ala Ser Asn His Lys Arg Arg Glu Pro Val Gly Gln Asp Ala
            20                  25                  30

Val Gly Leu Lys Asn Leu Ser Val Gln Val Ser Glu Ala Asn Leu Ile
        35                  40                  45

Gly Thr Gly Thr Ser Glu His Trp Val Asp Asp Glu Gly Pro Gln Pro
    50                  55                  60

Lys Lys Val Lys Ala Glu Asp Glu Ala Leu Leu Ser Glu Glu Asp Asp
65                  70                  75                  80

Pro Ile Asp Arg Arg Pro Trp Thr Gln Gln His Leu Glu Ala Ala Asp
                85                  90                  95

Ile Arg Arg Thr Pro Ser Leu Ala Leu Thr Pro Pro Gln Ala Glu Gln
            100                 105                 110

Glu Val Asp Val Leu Asp Val Asn Val Arg Gly Pro Asp Gly Cys Thr
        115                 120                 125

Pro Leu Met Leu Ala Ser Leu Arg Gly Gly Ser Ser Asp Leu Ser Asp
    130                 135                 140

Glu Asp Glu Asp Ala Glu Asp Ser Ser Ala Asn Ile Ile Thr Asp Leu
145                 150                 155                 160

Val Tyr Gln Gly Ala Ser Leu Gln Ala Gln Thr Asp Arg Thr Gly Glu
                165                 170                 175

Met Ala Leu His Leu Ala Ala Arg Tyr Ser Arg Ala Asp Ala Ala Lys
            180                 185                 190

Arg Leu Leu Asp Ala Gly Ala Asp Ala Asn Ala Gln Asp Asn Met Gly
        195                 200                 205

Arg Cys Pro Leu His Ala Ala Val Ala Ala Asp Ala Gln Gly Val Phe
    210                 215                 220

Gln Ile Leu Ile Arg Asn Arg Val Thr Asp Leu Asp Ala Arg Met Asn
225                 230                 235                 240

Asp Gly Thr Thr Pro Leu Ile Leu Ala Ala Arg Leu Ala Val Glu Gly
                245                 250                 255

Met Val Ala Glu Leu Ile Asn Cys Gln Ala Asp Val Asn Ala Val Asp
            260                 265                 270

Asp His Gly Lys Ser Ala Leu His Trp Ala Ala Ala Val Asn Asn Val
        275                 280                 285

Glu Ala Thr Leu Leu Leu Leu Lys Asn Gly Ala Asn Arg Asp Met Gln

```
            290                 295                 300
Asp Asn Lys Glu Glu Thr Pro Leu Phe Leu Ala Ala Arg Glu Gly Ser
305                 310                 315                 320

Tyr Glu Ala Ala Lys Ile Leu Leu Asp His Phe Ala Asn Arg Asp Ile
                325                 330                 335

Thr Asp His Met Asp Arg Leu Pro Arg Asp Val Ala Arg Asp Arg Met
            340                 345                 350

His His Asp Ile Val Arg Leu Leu Asp Glu Tyr Asn Val Thr Pro Ser
        355                 360                 365

Pro Pro Gly Thr Val Leu Thr Ser Ala Leu Ser Pro Val Ile Cys Gly
370                 375                 380

Pro Asn Arg Ser Phe Leu Ser Leu Lys His Thr Pro Met Gly Lys Lys
385                 390                 395                 400

Ser Arg Arg Pro Ser Ala Lys Ser Thr Met Pro Thr Ser Leu Pro Asn
                405                 410                 415

Leu Ala Lys Glu Ala Lys Asp Ala Lys Gly Ser Arg Arg Lys Lys Ser
            420                 425                 430

Leu Ser Glu Lys Val Gln Leu Ser Glu Ser Ser Val Thr Leu Ser Pro
        435                 440                 445

Val Asp Ser Leu Glu Ser Pro His Thr Tyr Val Ser Asp Thr Thr Ser
450                 455                 460

Ser Pro Met Ile Thr Ser Pro Gly Ile Leu Gln Ala Ser Pro Asn Pro
465                 470                 475                 480

Met Leu Ala Thr Ala Ala Pro Ala Pro Val His Ala Gln His Ala
                485                 490                 495

Leu Ser Phe Ser Asn Leu His Glu Met Gln Pro Leu Ala His Gly Ala
            500                 505                 510

Ser Thr Val Leu Pro Ser Val Ser Gln Leu Leu Ser His His Ile
        515                 520                 525

Val Ser Pro Gly Ser Gly Ser Ala Gly Ser Leu Ser Arg Leu His Pro
530                 535                 540

Val Pro Val Pro Ala Asp Trp Met Asn Arg Met Glu Val Asn Glu Thr
545                 550                 555                 560

Gln Tyr Asn Glu Met Phe Gly Met Val Leu Ala Pro Ala Glu Gly Thr
                565                 570                 575

His Pro Gly Ile Ala Pro Gln Ser Arg Pro Pro Glu Gly Lys His Ile
            580                 585                 590

Thr Thr Pro Arg Glu Pro Leu Pro Pro Ile Val Thr Phe Gln Leu Ile
        595                 600                 605

Pro Lys Gly Ser Ile Ala Gln Pro Ala Gly Ala Pro Gln Pro Gln Ser
610                 615                 620

Thr Cys Pro Pro Ala Val Ala Gly Pro Leu Pro Thr Met Tyr Gln Ile
625                 630                 635                 640

Pro Glu Met Ala Arg Leu Pro Ser Val Ala Phe Pro Thr Ala Met Met
                645                 650                 655

Pro Gln Gln Asp Gly Gln Val Ala Gln Thr Ile Leu Pro Ala Tyr His
            660                 665                 670

Pro Phe Pro Ala Ser Val Gly Lys Tyr Pro Thr Pro Ser Gln His
        675                 680                 685

Ser Tyr Ala Ser Ser Asn Ala Ala Glu Arg Thr Pro Ser His Ser Gly
690                 695                 700

His Leu Gln Gly Glu His Pro Tyr Leu Thr Pro Ser Pro Glu Ser Pro
705                 710                 715                 720
```

```
Asp Gln Trp Ser Ser Ser Ser Pro His Ser Ala Ser Asp Trp Ser Asp
                725                 730                 735

Val Thr Thr Ser Pro Thr Pro Gly Gly Ala Gly Gly Gly Gln Arg Gly
                740                 745                 750

Pro Gly Thr His Met Ser Glu Pro Pro His Asn Asn Met Gln Val Tyr
            755                 760                 765

Ala

<210> SEQ ID NO 4
<211> LENGTH: 24
<212> TYPE: DNA
<213> ORGANISM: Homo sapiens

<400> SEQUENCE: 4
cacagaggct gggaaaggat gata                                          24

<210> SEQ ID NO 5
<211> LENGTH: 23
<212> TYPE: DNA
<213> ORGANISM: Homo sapiens

<400> SEQUENCE: 5
ggccacctga agggaagcac ata                                           23
```